(12) United States Patent
Mitsunaga et al.

(10) Patent No.: US 10,717,781 B2
(45) Date of Patent: Jul. 21, 2020

(54) NEUROINVASION INHIBITOR

(75) Inventors: Shuichi Mitsunaga, Chiba (JP); Atsushi Ochiai, Chiba (JP)

(73) Assignees: National Cancer Center, Tokyo (JP); Chugai Seiyako Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/996,162

(22) PCT Filed: Jun. 5, 2009

(86) PCT No.: PCT/JP2009/060314
§ 371 (c)(1),
(2), (4) Date: Mar. 7, 2011

(87) PCT Pub. No.: WO2009/148148
PCT Pub. Date: Dec. 10, 2009

(65) Prior Publication Data
US 2011/0150869 A1 Jun. 23, 2011

(30) Foreign Application Priority Data
Jun. 5, 2008 (JP) ................. 2008-147944

(51) Int. Cl.
*A61K 39/00* (2006.01)
*C07K 16/28* (2006.01)
(52) U.S. Cl.
CPC .. *C07K 16/2866* (2013.01); *A61K 39/001119* (2018.08); *A61K 2039/505* (2013.01); *C07K 2317/24* (2013.01); *C07K 2317/76* (2013.01)
(58) Field of Classification Search
CPC ............ C07K 16/2866; C07K 2317/24; C07K 2317/76; A61K 2039/505; A61K 39/00; A61K 39/395; A61K 39/001119
See application file for complete search history.

(56) References Cited

U.S. PATENT DOCUMENTS

| 5,216,128 | A | | 6/1993 | Novick et al. |
|---|---|---|---|---|
| 5,530,101 | A | | 6/1996 | Queen et al. |
| 5,621,077 | A | | 4/1997 | Novick et al. |
| 5,639,455 | A | | 6/1997 | Shimamura et al. |
| 5,670,373 | A | | 9/1997 | Kishimoto |
| 5,795,965 | A | | 8/1998 | Tsuchiya et al. |
| 5,817,790 | A | | 10/1998 | Tsuchiya et al. |
| 5,856,135 | A | | 1/1999 | Tsuchiya et al. |
| 5,888,510 | A | | 3/1999 | Kishimoto et al. |
| 6,074,643 | A | * | 6/2000 | Barbera-Guillem ....... 424/178.1 |
| 6,121,423 | A | | 9/2000 | Tsuchiya et al. |
| 6,261,560 | B1 | | 7/2001 | Tsujinaka et al. |
| 6,552,083 | B1 | | 4/2003 | Isobe et al. |
| 6,723,319 | B1 | | 4/2004 | Ito et al. |
| 7,291,721 | B2 | | 11/2007 | Giles-Komar et al. |
| 7,320,792 | B2 | | 1/2008 | Ito et al. |
| 7,414,024 | B2 | | 8/2008 | Blay et al. |
| 7,479,543 | B2 | | 1/2009 | Tsuchiya et al. |
| 7,521,052 | B2 | | 4/2009 | Okuda et al. |
| 7,781,617 | B2 | | 8/2010 | Kudou et al. |
| 7,824,674 | B2 | | 11/2010 | Ito et al. |
| 8,226,611 | B2 | | 7/2012 | Chen et al. |
| 8,470,316 | B2 | | 6/2013 | Yasunami |
| 8,562,991 | B2 | | 10/2013 | Igawa et al. |
| 8,623,355 | B2 | | 1/2014 | Okada et al. |
| 8,736,401 | B2 | | 5/2014 | Kanno et al. |
| 8,771,686 | B2 | | 7/2014 | Ishida |
| 9,017,677 | B2 | | 4/2015 | Mihara |
| 2001/0001663 | A1 | | 5/2001 | Kishimoto et al. |
| 2002/0119150 | A1 | | 8/2002 | Kirk et al. |
| 2004/0018540 | A1 | | 1/2004 | Yamamura et al. |
| 2004/0170626 | A1 | | 9/2004 | Schuurman et al. |
| 2005/0096257 | A1 | | 5/2005 | Shima et al. |
| 2005/0142635 | A1 | | 6/2005 | Tsuchiya et al. |
| 2005/0158317 | A1 | | 7/2005 | Blay et al. |
| 2005/0182007 | A1 | | 8/2005 | McSwiggen et al. |
| 2006/0039902 | A1 | | 2/2006 | Young et al. |
| 2006/0111316 | A1 | | 5/2006 | Lawless |
| 2006/0165696 | A1 | | 7/2006 | Okano et al. |
| 2006/0188502 | A1 | * | 8/2006 | Giles-Komar et al. .... 424/145.1 |
| 2006/0193772 | A1 | * | 8/2006 | Ochiai et al. ................ 424/1.49 |

(Continued)

FOREIGN PATENT DOCUMENTS

| CN | 1164194 A | 11/1995 |
|---|---|---|
| CN | 1297357 A | 5/2001 |

(Continued)

OTHER PUBLICATIONS

Idezawa et al., (Yamanashi Med J. 2004;19(2):53-67).*
Ceyhan et al., (Biochem Biophys Res Commun. Sep. 26, 2008;374(3):442-7. Epub Jul. 18, 2008).*
Kayahara et al., (Pancreas. Oct. 2007;35(3):218-23).*
Unverified English language translation of: Idezawa, T., et al., "Interleukin-6 Functions as an Autocrine Invasion Factor of Human Pancreatic Cancer Cells," *Yamanashi Med. J.* 20(2):xxxvi, University of Yamanashi, Japan (2005).

(Continued)

*Primary Examiner* — Daniel E Kolker
*Assistant Examiner* — Bruce D. Hissong
(74) *Attorney, Agent, or Firm* — Nixon & Vanderyhe P.C.

(57) ABSTRACT

The present inventors discovered that neural invasion is suppressed by inhibiting IL-6 in a model for neural invasion of pancreatic cancer, and completed the present invention. The present inventors also demonstrated that: an IL-6 receptor is expressed in cells of human pancreatic cancer cell lines; and IL-6 enhances the chemotactic and migratory activities and intracellular signaling of pancreatic cancer cells; and thus pancreatic cancer can be treated by inhibiting IL-6. Furthermore, the present inventors found that neural invasion of human pancreatic cancer can be suppressed, from the results of administering IL-6 inhibitors to neural invasion model mice.

10 Claims, 9 Drawing Sheets
Specification includes a Sequence Listing.

(56) References Cited

U.S. PATENT DOCUMENTS

| | | |
|---|---|---|
| 2006/0251653 A1 | 11/2006 | Okuda et al. |
| 2006/0292147 A1 | 12/2006 | Yoshizaki et al. |
| 2007/0036785 A1* | 2/2007 | Kishimoto et al. ........ 424/143.1 |
| 2007/0134242 A1 | 6/2007 | Nishimoto et al. |
| 2007/0167425 A1 | 7/2007 | Nakade et al. |
| 2008/0081041 A1 | 4/2008 | Nemeth |
| 2009/0022719 A1 | 1/2009 | Mihara et al. |
| 2009/0022726 A1 | 1/2009 | Zaki et al. |
| 2009/0028784 A1 | 1/2009 | Garcia-Martinez et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2010/0008907 A1 | 1/2010 | Nishimoto et al. |
| 2010/0034811 A1 | 2/2010 | Ishida |
| 2010/0061986 A1 | 3/2010 | Takahashi et al. |
| 2010/0129357 A1 | 5/2010 | Garcia-Martinez et al. |
| 2010/0298542 A1 | 11/2010 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga et al. |
| 2011/0245473 A1 | 10/2011 | Igawa et al. |
| 2012/0045453 A1 | 2/2012 | Chen et al. |
| 2012/0183539 A1 | 7/2012 | Maeda |
| 2013/0202588 A1 | 8/2013 | Nishimura |
| 2016/0139117 A1 | 5/2016 | Yamamura et al. |
| 2018/0149573 A1 | 5/2018 | Yamamura et al. |

FOREIGN PATENT DOCUMENTS

| | | | |
|---|---|---|---|
| CN | 1694894 A | 11/2005 | |
| CN | 1849135 A | 10/2006 | |
| EP | 0 628 639 A1 | 12/1994 | |
| EP | 0 721 783 A1 | 7/1996 | |
| EP | 0 783 893 A1 | 7/1997 | |
| EP | 0 791 359 A1 | 8/1997 | |
| EP | 0791359 | 8/1997 | |
| EP | 0 811 384 A1 | 12/1997 | |
| EP | 0931544 A2 | 7/1999 | |
| EP | 0 983 767 A1 | 3/2000 | |
| EP | 1 074 268 A1 | 2/2001 | |
| EP | 1 108 435 A1 | 6/2001 | |
| EP | 1 197 210 A1 | 4/2002 | |
| EP | 1 374 900 A1 | 1/2004 | |
| EP | 1 562 968 | 5/2004 | |
| EP | 1 690 550 A1 | 8/2006 | |
| EP | 1 707 215 A1 | 10/2006 | |
| EP | 1 941 907 A1 | 7/2008 | |
| EP | 1 967 207 A1 | 9/2008 | |
| EP | 1 967 209 A1 | 9/2008 | |
| EP | 1 990 060 A1 | 11/2008 | |
| EP | 2 025 346 A1 | 2/2009 | |
| EP | 2 305 306 A1 | 4/2011 | |
| EP | 2 578 233 A1 | 4/2013 | |
| EP | 2639305 A1 | 9/2013 | |
| ES | 2276525 T3 | 6/2007 | |
| FR | 2 694 767 A1 | 2/1994 | |
| JP | 6-237772 A | 8/1994 | |
| JP | 07-046998 A | 2/1995 | |
| JP | H07-505609 | 6/1995 | |
| JP | 08-208514 A | 8/1996 | |
| JP | 8-208514 A | 8/1996 | |
| JP | 11-180873 A | 7/1999 | |
| JP | 2002-527354 A | 8/2002 | |
| JP | 2004-28926 A | 1/2004 | |
| JP | 2005-524606 A | 8/2005 | |
| JP | 2005-281235 A | 10/2005 | |
| JP | 2006-524685 A | 11/2006 | |
| JP | 2007-528691 A | 10/2007 | |
| JP | 2008-37875 A | 2/2008 | |
| JP | 2008-37876 A | 2/2008 | |
| JP | 2008-538931 A | 11/2008 | |
| JP | 2008-297315 A | 12/2008 | |
| JP | 2010-527615 A | 8/2010 | |
| RU | 2127117 C1 | 3/1999 | |
| RU | 2430111 C1 | 9/2009 | |
| TW | 2008/03895 A | 1/2008 | |
| TW | 201021829 A1 | 6/2010 | |
| WO | WO 92/019759 A1 | 11/1992 | |
| WO | WO 93/08817 A1 | 5/1993 | |
| WO | WO 94/20488 A1 | 9/1994 | |
| WO | WO 94/28159 A1 | 12/1994 | |
| WO | WO 95/009873 A1 | 4/1995 | |
| WO | WO 96/11020 A1 | 4/1996 | |
| WO | WO 96/12503 A1 | 5/1996 | |
| WO | WO 96/25174 A1 | 8/1996 | |
| WO | WO 98/36061 A2 | 8/1998 | |
| WO | WO 98/42377 A1 | 10/1998 | |
| WO | WO 99/47170 A1 | 9/1999 | |
| WO | WO 99/60013 A2 | 11/1999 | |
| WO | WO 00/10607 A1 | 3/2000 | |
| WO | WO 01/005394 A1 | 1/2001 | |
| WO | WO 01/45678 A2 | 6/2001 | |
| WO | WO 02/03492 A1 | 1/2002 | |
| WO | WO 02/080969 A1 | 10/2002 | |
| WO | WO 03/048205 A2 | 6/2003 | |
| WO | WO 03/105861 A1 | 12/2003 | |
| WO | WO 2004/007701 A1 | 1/2004 | |
| WO | WO 2004/039826 A1 | 5/2004 | |
| WO | WO 2004/045507 A2 | 6/2004 | |
| WO | WO 2004/045512 A2 | 6/2004 | |
| WO | WO 2004/071404 A2 | 8/2004 | |
| WO | WO 2004/073741 A1 | 9/2004 | |
| WO | WO 2004/096273 A1 | 11/2004 | |
| WO | WO 2005/028514 A1 | 3/2005 | |
| WO | WO 2005/037315 A1 | 4/2005 | |
| WO | WO 2005/044848 A1 | 5/2005 | |
| WO | WO 2005/061000 A1 | 7/2005 | |
| WO | WO 2005/107800 A1 | 11/2005 | |
| WO | WO 2006/009092 A1 | 1/2006 | |
| WO | WO 2006/070286 A2 | 7/2006 | |
| WO | WO 2006/072954 A2 | 7/2006 | |
| WO | WO 2006/119115 A2 | 11/2006 | |
| WO | WO 2007/043641 A1 | 4/2007 | |
| WO | WO 2007/046489 A1 | 4/2007 | |
| WO | WO 2007/058194 A1 | 5/2007 | |
| WO | WO 2007/061029 A1 | 5/2007 | |
| WO | WO 2007/067976 A2 | 6/2007 | |
| WO | WO 2007/076927 A1 | 7/2007 | |
| WO | WO 2007/086490 A1 | 8/2007 | |
| WO | WO 2007/116962 A1 | 10/2007 | |
| WO | WO 2007/143168 A2 | 12/2007 | |
| WO | WO 2008/020079 A1 | 2/2008 | |
| WO | WO 2008/090901 A1 | 7/2008 | |
| WO | WO 2008/144763 A2 | 11/2008 | |
| WO | WO 2009/010539 A2 | 1/2009 | |
| WO | WO 2009/041613 A1 | 4/2009 | |
| WO | WO 2009/041621 A1 | 4/2009 | |
| WO | WO 2009/125825 A1 | 10/2009 | |
| WO | WO 2009/148148 A1 | 12/2009 | |
| WO | WO 2010/035769 A1 | 4/2010 | |
| WO | WO 2010/107108 A1 | 9/2010 | |
| WO | WO 2011/013786 A1 | 2/2011 | |
| WO | WO 2011/149051 A1 | 12/2011 | |
| WO | WO-201206387 A1 | 5/2012 | |
| WO | WO 2012/118750 A2 | 9/2012 | |
| WO | WO 2014/200018 A1 | 12/2014 | |
| WO | WO-2016186154 A1 | 11/2016 | |

OTHER PUBLICATIONS

Unverified English language translation of: Kamohara, H., et al., "IL-6 no Suigan Saibo no Zoshoku-Ten'i Oyobosu Eikyo to Kanshitsu Saibo ni yoru Hatsugen Seigyo Kiko," *Japanese Journal of Gastroenterological Surgery* 39(7): 1356 (Abstract 2529), Japanese Journal of Gastroenterological Surgery, Japan (2006).

Amendment in Reply to Office Action dated May 3, 2011, submitted Nov. 1, 2011, in U.S. Appl. No. 12/090,061, Yasunami, Y., el al., filed Oct. 13, 2006.

Alvarez, B., et al., "Tumor necrosis factor-α exerts interleukin-6-dependent and -independent effects on cultured skeletal muscle cells," *Biochim. et Biophysica Acta* 1542:66-72, Elsevier Science B.V., Netherlands (2002).

(56) References Cited

OTHER PUBLICATIONS

Barton-Davis, E.R., et al., "Viral mediated expression of insulin-like growth factor I blocks the aging-related loss of skeletal muscle function," *Proc. Natl. Acad. Sci. USA* 95:15603-15607, The National Academy of Sciences, United States (1998).
Bogdanovich, S., et al., "Functional improvement of dystrophic muscle by myostatin blockade," *Nature* 420:418-421, Nature Publishing Group, England (2002).
Bork, P., "Powers and Pitfalls in Sequence Analysis: The 70% Hurdle," *Genome Research* 10:398-400, Cold Spring Harbor Laboratory Press, United States (2000).
Brenner, S.E., "Errors in genome annotation," *Trends in Genetics* 15:132-133, Elsevier Science, United States (1999).
Dangott, B., et al., "Dietary creatine monohydrate supplementation increases satellite cell mitotic activity during compensatory hypertrophy," *Int. J. Sports Med.* 21:13-16, Georg Thieme Verlag, Germany (2000).
Darr, K.C. and Schultz, E., "Hindlimb suspension suppresses muscle growth and satellite cell proliferation," *J. Appl. Physiol.* 67:1827-1834, American Physiological Society, United States (1989).
Doerks, T., "Protein annotation: detective work for function prediction," *Trends in Genetics* 142:248-250, Elsevier Science Ltd., United States (1998).
Fisniku, O., et al., "Protective effects of PG490-88 on chronic allograft rejection by changing intragraft gene expression profiles," *Transplantation Proceedings* 37:1962-1964, Elsevier Inc., United States (2005).
Fredj, S., et al., "Role of interleukin-6 in cardiomyocyte/cardiac fibroblast interactions during myocyte hypertrophy and fibroblast proliferation," *J. Cell. Physiol.* 204:428-436, Wiley-Liss, Inc., United States (2005).
Garry, D.J., et al., "Persistent expression of MNF identifies myogenic stem cells in postnatal muscles," *Developmental Biology* 188:280-294, Academic Press, United States (1997).
Garry, D.J., et al., "Myogenic stem cell function is impaired in mice lacking the forkhead/winged helix protein MNF," *Proc. Natl. Acad. Sci. USA* 97:5416-5421, National Academy of Sciences, United States (2000).
Guice, K.S., et al., "Anti-tumor necrosis factor antibody augments edema formation in caerulein-induced acute pancreatitis," *Journal of Surgical Research* 51:495-499, Academic Press, Inc., United States (1991).
Hocking, D.C., et al., "Mechanisms of pulmonary edema induced by tumor necrosis factor-α," *Circulations Research* 67:68-77, American Heart Association, United States (1990).
Jejurikar, S.S., et al., "Skeletal muscle denervation increases satellite cell susceptibility to apoptosis," *Plast. Reconstr. Surg.* 110:160-168, Lippincott Williams & Wilkins, United States (2002).
Kami, K., et al., "Gene expression of receptors for IL-6, LIF, and CNTF in regenerating skeletal muscles," *J. Histochem. Cytochem.* 48:1203-1213, The Histochemical Society, Inc., United States (2000).
Knulst, A.C., et al., "Cytokine detection and modulation in acute graft vs. host disease in mice," *Mediators of Inflammation* 3:33-40, Hindawi Publishing Corporation, United States (1994).
Kobara, M., et al., "Antibody against interleukin-6 receptor attenuates left ventricula remodelling after myocardial infarction in mice," *Cardiovascular Research* 87:424-430, European Society of Cardiology, France (2010).
Kurek, J.B., et al., "Up-regulation of leukaemia inhibitory factor and interleukin-6 in transected sciatic nerve and muscle following denervation," *Neuromusc. Disord.* 6:105-114, Elsevier Science Ltd., Great Britain (1996).
Kurek, J.B., et al., "The role of leukemia inhibitory factor in skeletal muscle regeneration," *Muscle & Nerve* 20:815-822, John Wiley & Sons, Inc., United States (1997).
Matsuda, T., et al., "Establishment of an interleukin 6 (IL 6)/B cell stimulatory factor 2-dependent cell line and preparation of anti-IL 6 monoclonal antibodies," *Eur. J. Immunol.* 18:951-956, VCH Verlagsgesellschaft mbH, Germany (1988).

Matsushita, K., et al., "Interleukin-6/soluble interleukin-6 receptor complex reduces infarct size via inhibiting myocardial apoptosis," *Laboratory Investigation* 85:1210-1223, U.S. and Canadian Academy of Pathology, Inc., United States (2005).
Mauro, A., "Satellite cell of skeletal muscle fibers," *J. Biophys. Biochem. Cytol.* 9:493-495, Rockefeller Institute for Medical Research, United States (1961).
McCormick, K.M. and Schultz, E., "Role of satellite cells in altering myosin expression during avian skeletal muscle hypertrophy," *Developmental Dynamics* 199:52-63, Wiley-Liss, Inc., United States (1994).
Moss, F.P. and Leblond, C.P., "Satellite cells as the source of nuclei in muscles of growing rats," *Anat. Rec.* 170:421-436, A.R. Liss, United States (1971).
Mozdziak, P.E., et al., "Quantitation of satellite cell proliferation in vivo using image analysis," *Biotechnic & Histochemistry* 69:249-252, Williams & Wilkins, England (1994).
Mozdziak, P.E., et al., "Hindlimb suspension reduces muscle regeneration," *Eur. J. Appl. Physiol.* 78:136-140, Springer-Verlag, Germany (1998).
Mozdziak, P.E., et al., "Unloading of juvenile muscle results in a reduced muscle size 9 wk after reloading," *J. Appl. Physiol.* 88:158-164, American Physiological Society, United States (2000).
Mozdziak, P.E., et al., "Muscle regeneration during hindlimb unloading results in a reduction in muscle size after reloading," *J. Appl. Physiol.* 91:183-190, American Physiological Society, United States (2001).
Mukaida, N., et al., "Cytokines and immune network," *Rinsho Kensa* 35:447-452, Japan (1991).
Murata et al., "Development mechanism and pathophysiology," *The Saishin-Igaku* 47:49-56, Japan (1992).
Murphy, R., et al., "The effect of mechanical stretch on proliferation and differentiation of C2C12 cells," *Experimental Biology 2004: Meeting Abstracts*: A743, Abstract No. 476.6, American Association of Immunologists, United States (2004).
Ngo, J.T., et al., Computational Complexity, Protein Structure Prediction, and the Levinthal Paradox, in The Protein Folding Problem and Tertiary Structure Prediction 433-440 and 492-495 (Merz, K. and Le Grand, S. ed., 1994).
Phillips, A.J., "The challenge of gene therapy and DNA delivery," *J. Pharmacy and Pharmacology* 53:1169-1174, John Wiley & Sons, Inc., United Kingdom (2001).
Pirollo, K.F. and Chang, E.H., "Targeted Delivery of Small Interfering RNA: Approaching Effective Cancer Therapies," *Cancer Res.* 68:1247-1250, American Association for Cancer Research, United States (2008).
Quentmeier, H., et al., "Role of IL-6, IL-2, and IL-4 in the in vitro induction of cytotoxic T cells," *J. Immunology* 149:3316-3320, The American Association of Immunologists, United States (1992).
Schultz, E., et al., "Response of satellite cells to focal skeletal muscle injury," *Muscle & Nerve* 8:217-222, John Wiley & Sons, Inc., United States (1985).
Schultz, E., et al., "Acute effects of hindlimb unweighting on satellite cells of growing skeletal muscle," *J. Appl. Physiol.* 76:266-270, American Physiological Society, United States (1994).
Schultz, E., "Satellite cell proliferative compartments in growing skeletal muscles," *Developmental Biology* 175:84-94, Academic Press, Inc., United States (1996).
Shimizu, H., et al., "KRP-203, a novel synthetic immunosuppressant, prolongs graft survival and attenuates chronic rejection in rat skin and heart allografts," *Circulation* 111:222-229, American Heart Association, Inc., United States (2005).
Shimizu, K. and Oku, N., "Cancer anti-angiogenic therapy," *Biol. Pharm. Bull.* 27:599-605, Pharmaceutical Society of Japan, Japan (2004).
Skolnick, J. and Fetrow, J.S., "From genes to protein structure and function: novel applications of computational approaches in the genomic era," *Trends in Biotechnology* 18:34-39, Elsevier Science Ltd., United States (2000).
Snow, M.H., "Myogenic cell formation in regenerating rat skeletal muscle injured by mincing. II. An autoradiographic study." *Anat. Rec.* 188:201-217, A.R. Liss, United States (1977).

(56) References Cited

OTHER PUBLICATIONS

Snow, M.H., "Satellite cell response in rat soleus muscle undergoing hypertrophy due to surgical ablation of synergists," *Anat. Rec.* 227:437-446, Wiley-Liss, Inc., United States (1990).

Stan A.C., et al., "In vivo inhibition of angiogenesis and growth of the human U-87 malignant glial tumor by treatment with an antibody against basic fibroblast growth factor," *J. Neurosurg.* 82:1044-1052, American Association of Neurosurgeons, United States (1995).

Tamura, T., et al., "Soluble interleukin-6 receptors triggers osteoclast formation by interleukin 6," *Proc. Natl. Acad. Sci. USA* 90:11924-11928, Cell Biology (1993).

Tobe, T., et al., "Targeted disruption of the FGF2 gene does not prevent choroidal neovascularization in a murine model," *Am. J. Pathol.* 153:1641-1646, American Society for Investigative Pathology, United States (1998).

Tsujinaka, T., et al., "Interleukin 6 receptor antibody inhibits muscle atrophy and modulates proteolytic systems in interleukin 6 transgenic mice," *J. Clin. Invest.* 97:244-249, The American Society for Clinical Investigation, United States (1996).

Ulich, T.R., et al., "Intratracheal injection of endotoxin and cytokines," *Am. J. Pathol.* 138:1097-1101, American Association of Pathologists, United States (1991).

Unverified English language translation of Mukaida, N., et al., "Cytokines and immune network," *Rinsho Kensa* 35:447-452, Japan (1991).

Unverified English language translation of Murata et al., "Development mechanism and pathophysiology," *The Saishin-Igaku* 47:49-56, Japan (1992).

Vidal, L., et al., "Making sense of antisense," *European J Cancer* 41:2812-2818, Elsevier Ltd., United States (2005).

Wang, X.D., et al., "Mechanical load-dependent regulation of satellite cell and fiber size in rat soleus muscle," *Am. J. Physiol. Cell. Physiol.* 290:C981-C989, American Physiological Society, United States (2006).

Warren, G.L., et al., "Physiological role of tumor necrosis factor α in traumatic muscle injury," *FASEB J.* 16:1630-1632, The Federation of American Societies for Experimental Biology, United States (2002).

Wells, J.A., "Additivity of Mutational Effects in Proteins," *Biochemistry* 29:8509-8517, American Chemical Society, United States (1990).

Restriction Requirement in U.S. Appl. No. 12/090,676, Kobara, M., et al., filed Oct. 20, 2006, dated Mar. 12, 2010, U.S. Patent and Trademark Office, Alexandria, VA.

Restriction Requirement in U.S. Appl. No. 12/085,065, Okada, M., et al., filed Nov. 15, 2006, dated April 30, 2010, U.S. Patent and Trademark Office, Alexandria, VA.

Restriction Requirement in U.S. Appl. No. 12/090,061, Yasunami, Y., et al., filed Oct. 13, 2006, dated Aug. 27, 2010, U.S. Patent and Trademark Office, Alexandria, VA.

Restriction Requirement in U.S. Appl. No. 12/296,193, Nishimoto, N., et al., filed Apr. 6, 2007, dated Oct. 5, 2010, U.S. Patent and Trademark Office, Alexandria, VA.

Office Action in U.S. Appl. No. 12/090,676, Kobara, M., et al., filed Oct. 20, 2006, dated Oct. 6, 2010, U.S. Patent and Trademark Office, Alexandria, VA.

Patel, N.S.A., et al., "Endogenous Interleukin-6 Enhances the Renal Injury, Dysfunction, and Inflammation Caused by Ischemia/Reperfusion," *J. Pharmacol. Exp. Ther.* 312(3):1170-1178, The American Society for Pharmacology and Experimental Therapeutics, United States (2005).

Unverified English language translation of: Skurkovich, S.V., et al., "Anticytokine therapy—new approach to the treatment of autoimmune and cytokine-disturbance diseases," *Oncology and Immunopathology* 2:71-80 (2003) (relevant parts).

Skurkovich, S.V., et al., "Anticytokine therapy—new approach to the treatment of autoimmune and cytokine-disturbance diseases," *Oncology and Immunopathology* 2:71-80 (2003) (Russian).

Office Action dated Sep. 26, 2011, in U.S. Appl. No. 12/094,644, Nakashima, J., et al., filed Nov. 24, 2006, U.S. Patent and Trademark Office, Alexandria, VA.

Office Action dated Aug. 16, 2011, in U.S. Appl. No. 12/161,733, Ishida, S., filed Jan. 26, 2007, U.S. Patent and Trademark Office, Alexandria, VA.

Office Action dated Aug. 29, 2011, in U.S. Appl. No. 12/524,041, Takahashi, M., et al., filed Jan. 23, 2008, U.S. Patent and Trademark Office, Alexandria, VA.

Office Action dated April 11, 2012, in U.S. Appl. No. 12/085,065, inventors Okada, M., et al., filed Nov. 15, 2006, U.S. Patent and Trademark Office, Alexandria, VA.

Office Action dated Jan. 12, 2012, in U.S. Appl. No. 12/090,061, inventors Yasunami, Y., et al., filed Oct. 13, 2006, U.S. Patent and Trademark Office, Alexandria, VA.

Response to Restriction Requirement filed Aug. 31, 2010, in U.S. Appl. No. 12/090,676, inventors Kobara, M., et al., filed Oct. 20, 2006, U.S. Patent and Trademark Office, Alexandria, VA.

Amendment and Reply to Office Action submitted Mar. 21, 2012, in U.S. Appl. No. 12/094,644, inventors Nakashima, J., et al., filed Nov. 24, 2006, U.S. Patent and Trademark Office, Alexandria, VA.

Amendment and Reply to Office Action submitted Feb. 15, 2012, in U.S. Appl. No. 12/161,733, inventor Ishida, S., filed Jan. 26, 2007, U.S. Patent and Trademark Office, Alexandria, VA.

Office Action dated Apr. 9, 2012, in U.S. Appl. No. 12/161,733, inventor Ishida, S., filed Jan. 26, 2007, U.S. Patent and Trademark Office, Alexandria, VA.

Amendment and Reply to Office Action submitted Jan. 26, 2012, in U.S. Appl. No. 12/296,193, inventors Nishimoto, N., et al., filed Apr. 6, 2007, U.S. Patent and Trademark Office, Alexandria, VA.

Amendment and Reply to Office Action submitted Mar. 19, 2012, in U.S. Appl. No. 12/296,193, inventors Nishimoto, N., et al., filed April 6, 2007, U.S. Patent and Trademark Office, Alexandria, VA.

Response to Restriction Requirement filed Oct. 28, 2011, in U.S. Appl. No. 12/524,041, inventors Takahashi, M., et al., filed Jan. 23, 2008, U.S. Patent and Trademark Office, Alexandria, VA.

Office Action dated Dec. 21, 2011, in U.S. Appl. No. 12/524,041, inventors Takahashi, M., et al., filed Jan. 23, 2008, U.S. Patent and Trademark Office, Alexandria, VA.

Skurkovich, S.V., et al., "Anticytokine therapy—new approach to the treatment of autoimmune and cytokine-disturbance diseases," *Med. Hypotheses* 59(6):770-780, Eden Press, United States (2002) (English) (Relevant portions).

Skurkovich, S.V., et al., "Anticytokine therapy—new approach to the treatment of autoimmune and cytokine-disturbance diseases," *Med. Hypotheses* 59(6):770-780, Eden Press, United States (2002) (Russian).

Idezawa, T., et al., "Interleukin-6 Functions as an Autocrine Invasion Factor of Human Pancreatic Cancer Cells," *Yamanashi Med. J.* 19(2):53-67, University of Yamanashi, Japan (2004).

Idezawa, T., et al., "Interleukin-6 Functions as an Autocrine Invasion Factor of Human Pancreatic Cancer Cells," *Yamanashi Med. J.* 20(2):xxxvi, University of Yamanashi, Japan (2005).

Kamohara, H., et al., "IL-6 no Suigan Saibo no Zoshoku-Ten'i Oyobosu Eikyo to Kanshitsu Saibo ni yoru Hatsugen Seigyo Kiko," *Japanese Journal of Gastroenterological Surgery* 39(7):1356 (Abstract 2529), Japanese Journal of Gastroenterological Surgery, Japan (2006).

Extended European Search Report in European Patent Appl. No. 08 703 686.9, Applicants Shinshu University, et al., dated Aug. 24, 2010, European Patent Office, The Netherlands.

International Preliminary Report on Patentability with Written Opinion of the International Searching Authority for International Application No. PCT/JP2008/050842, dated Jul. 28, 2009, The International Bureau of WIPO, Switzerland.

Maeda, S. et al., "Role of IKKβ / NF-κB Activation for Development of Liver Metastasis," Supplement: The 58th Annual Meeting of the American Association for the Study of Liver Diseases, *Hepatol.* 46:Issue Supplement S1, AASLD Abstracts, p. 518A, abstract No. 630, American Association for the Study of Liver Diseases (2007).

Maeda, S. et al., "Essential Roles of Ikkβ / Nf-κB Activation for Development of Liver Metastasis in Mice," *Gastroenterol.* 130:P-1-P-350, Supplement 2, AASLD Abstracts, p. A-750, abstract No. 107, Elsevier Inc. (2006).

(56) References Cited

OTHER PUBLICATIONS

English language Database Abstract for JP 6-237772 A, published Aug. 30, 1994, European Patent Office, Espacenet, Worldwide Database.
English language Abstract for JP 8-208514 A, published Aug. 13, 1996, European Patent Office, Espacenet, Worldwide Database.
Ashizawa, T., et al., "Clinical significance of interleukin-6 (IL-6) in the spread of gastric cancer: role of IL-6 as a prognostic factor," *Gastric Cancer* 8:124-131, International and Japanese Gastic Cancer Associations, Japan (2005).
Beck, J.T., et al., "Brief report: alleviation of systemic manifestations of Castleman's disease by monoclonal anti-interleukin-6 antibody," *N. Engl. J. Med.* 330:602-605, United States (1994).
Bond, M., et al., "Synergistic upregulation of metalloproteinase-9 by growth factors and inflammatory cytokines: an absolute requirement for transcription factor NF-κb," *FEBS Letters* 435:29-34, Federation of European Biochemical Societies (1998).
Campo, S., et al., "Comparative Activity of Sant7 and anti-IL-6, IL-6R monoclonal antibodies in a murine model of B-cell lymphoma," *Cytokine* 31:368-374, Elsevier Ltd., Netherlands (2005).
Choy, E., "Inhibiting interleukin-6 in rheumatoid arthritis," *Curr. Rheumatol. Rep.* 10:413-417, Current Medicine Group LLC, United States (2008).
Ewert, S., et al., "Stability improvement of antibodies for extracellular and intracellular applications: CDR grafting to stable frameworks and structure-based framework engineering," *Methods* 34:184-199, Elsevier Inc., Netherlands (2004).
Gao, S. P., et al., "Mutations in the EGFR kinase domain mediate STAT3 activation via IL-6 production in human lung adenocarcinomas," *J. Clin. Invest.* 117(12):3846-3856, The American Society for Clinical Investigation, United States (2007).
Ghosh, S. and Karin, M., "Missing Pieces in the NF-κB Puzzle," *Cell* 109: S81-S96, Cell Press, United States (2002).
Greten, F. R., et al., "IKKβ Links Inflammation and Tumorigenesis in a Mouse Model of Colitis-Associated Cancer," *Cell* 118:285-296, Cell Press, United States (2004).
Guerne, P-A., et al., "Synovium as a source of interleukin 6 in vitro. Contribution to local and systemic manifestations of arthritis," *J. Clin. Invest.*, 83:585-592, The American Society for Clinical Investigation, Inc., United States (1989).
Guillén, I., et al., "Cytokine signaling during myocardial infarction: sequential appearance of IL-1β and IL-6," *Am. J. Physiol.* 269(2 Pt 2):R229-235, The American Physiological Society (1995).
Hanes, J., et al., "Picomolar affinity antibodies from a fully synthetic naive library selected and evolved by ribosome display," *Nat. Biotechnol.* 18:1287-1292, Nature America Inc. (2000).
Hirai, I., et al., "Perineural Invasion in Pancreatic Cancer," *Pancreas* 24(1):15-25, Lippincott Williams & Wilkins, Inc., United States (2002).
Hirano, T., et al., "Excessive production of interleukin 6/B cell stimulatory factor-2 in rheumatoid arthritis," *Eur. J. Immunol.* 18:1797-1801, VCH Verlagsgesellschaft mbH (1988).
Hirota, H., et al., "Loss of a gp130 Cardiac Muscle Cell Survival Pathway Is a Critical Event in the Onset of Heart Failure during Biomechanical Stress," *Cell* 97:189-198, Cell Press, United States (1999).
Houssiau, F.A., et al., "Interleukin-6 in synovial fluid and serum of patients with rheumatoid arthritis and other inflammatory arthritides," *Arthritis Rheum.* 31(6):784-788, John Wiley & Sons (1988).
Karin, M. and Lin, A., "NF-κB at the crossroads of life and death," *Nature Immunology* 3(3):221-227, Nature Publishing Group, England (2002).
Karin, M., et al., "NF-κB in Cancer: From Innocent Bystander to Major Culprit," *Nature Reviews Cancer* 2:301-310, Nature Publishing Group, England (2002).
Kishimoto, T., "The biology of interleukin-6," *Blood* 74(1):1-10, The American Society of Hematology, United States (1989).

Kotake, S., et al., "Interleukin-6 receptors in the synovial fluids from rheumatoid arthritis patients are responsible for osteoclast-like cell formation," *J. Bone Miner Res.* 11(1):88-95, Blackwell Science, Inc. (1996).
Madhok, R., et al., "Serum interleukin 6 levels in rheumatoid arthritis: correlations with clinical and laboratory indices of disease activity," *Ann. Rheum. Dis.* 52:232-234, BMJ Group, United Kingdom (1993).
Maeda, S., et al., "IKKβ Couples Hepatocyte Death to Cytokine-Driven Compensatory Proliferation that Promotes Chemical Hepatocarcinogenesis," *Cell* 121:977-990, Elsevier Inc., Netherlands (2005).
Maeda, S., et al., "Ikappa B Kinase β/Nuclear Factor-κB Activation Controls the Development of Liver Metastasis by Way of Interleukin-6 Expression," *Hepatology* 50(6):1851-1860, The American Association for the Study of Liver Diseases (2009).
Martignoni, M.E., et al., "Role of Mononuclear Cells and Inflammatory Cytokines in Pancreatic Cancer-Related Cachexia," *Clin. Cancer Res.* 11(16):5802-5808, American Association for Cancer Research (2005).
Matzaraki, V., et al., "Evaluation of serum procalcitonin and interleukin-6 levels as markers of liver metastasis," *Clinical Biochemistry* 40:336-342, Elsevier Inc., United States (2007).
Miyamoto, Y., et al., "Interleukin-6 Inhibits Radiation Induced Apoptosis in Pancreatic Cancer Cells," *Anticancer Research* 21:2449-2456 (2001).
Naugler, W. E., et al., "Gender Disparity in Liver Cancer Due to Sex Differences in MyD88-Dependent IL-6 Production," *Science* 317:121-124, American Association for the Advancement of Science, United States (2007).
Nishimoto, N., et al., "Interleukin 6: from bench to bedside," *Nat. Clin. Pract. Rheumatol.* 2(11):619-626, Nature Publishing Group, England (2006).
Okada, Y., et al., "Experimental Implication of Celiac Ganglionotropic Invasion of Pancreatic-Cancer Cells Bearing c-ret Proto-Oncogene With Reference to Glial-Cell-Line-Derived Neurotrophic Factor (GDNF)," *Int. J. Cancer* 81:67-73, Wiley-Liss, Inc. (1999).
Pikarsky, E., et al., "NF-κB functions as a tumour promoter in inflammation-associated cancer," *Nature* 431:461-466, Nature Publishing Group, England (2004).
Sack, U., et al., "Interleukin-6 in synovial fluid is closely associated with chronic synovitis in rheumatoid arthritis," *Rheumatol. Int.* 13:45-51, Springer-Verlag (1993).
Sansone, P., et al., "IL-6 triggers malignant features in mammospheres from human ductal breast carcinoma and normal mammary gland," *J. Clin. Invest.* 117(12):3988-4002, The American Society for Clinical Investigation, United States (2007).
Sarkar, F. H., et al., "Back to the Future: COX-2 Inhibitors for Chemoprevention and Cancer Therapy," *Mini-Reviews in Medicinal Chemistry* 7:599-608, Bentham Science Publishers Ltd., Netherlands (2007).
Steeg, P. S., "Tumor metastasis: mechanistic insights and clinical challenges," *Nature Medicine* 12(8):895-904, Nature Publishing Group, England (2006).
Steeg, P. S. and Theodorescu, D., "Metastasis: a therapeutic target for cancer," *Nature Clinical Practice Oncology* 5(4):206-219, Nature Publishing Group, England (2008).
Studebaker, A. W., et al., "Fibroblasts Isolated from Common Sites of Breast Cancer Metastasis Enhance Cancer Cell Growth Rates and Invasiveness in an Interleukin-6-Dependent Manner," *Cancer Res* 68(21):9087-9095, American Association for Cancer Research, United States (2008).
Takahashi, H., et al., "Antiproteases in Preventing the Invasive Potential of Pancreatic Cancer Cells," *J. Pancreas* 8(4 Suppl.):501-508 (2007).
Takeda, K., et al., "Murine Tumor Cells Metastasizing Selectively in the Liver: Ability to Produce Hepatocyte-activating Cytokines Interleukin-1 and/or -6," *Jpn. J. Cancer Res.* 82:1299-1308, John Wiley & Sons, Inc., United States (1991).
Tisdale, M.J., "Biology of cachexia," *J. Natl. Cancer Inst.* 89(23):1763-1773, Oxford University Press, England (1997).

(56) References Cited

OTHER PUBLICATIONS

Wilansky, S., "Echocardiography in the Assessment of Complications of Myocardial Infarction," *Tex. Heart Inst. J.* 18(4):237-242, Texas Heart Institute (1991).
Yamakawa, Y., et al., "Astrocytes Promote the Proliferation of Lung Cancer Cells in Brain Metastases via inflammatory cytokines, especially IL-6," *Neuroscience* 48:216, P-22 (poster presentation) (2009).
Amendment and Reply to Office Action submitted Oct. 9, 2012, in U.S. Appl. No. 12/085,065, inventors Okada, M., et al., filed Nov. 15, 2006, U.S. Patent and Trademark Office, Alexandria, VA.
Office Action dated Jan. 11, 2013, in U.S. Appl. No. 12/085,065, inventors Okada, M., et al., filed Nov. 15, 2006, U.S. Patent and Trademark Office, Alexandria, VA.
Amendment and Reply to Office Action submitted Jun. 11, 2012, in U.S. Appl. No. 12/090,061, inventor Yasunami, Y., filed Oct. 13, 2006, U.S. Patent and Trademark Office, Alexandria, VA.
Office Action dated May 22, 2012, in U.S. Appl. No. 12/094,644, inventors Nakashima J., et al., filed Nov. 24, 2006, U.S. Patent and Trademark Office, Alexandria, VA.
Co-pending U.S. Appl. No. 13/700,355, inventors Nishimura, T., et al., filed Nov. 27, 2012 (Not Yet Published).
International Search Report for International Application No. PCT/JP2010/062874, dated Aug. 31, 2010, Japanese Patent Office, Japan (Not a Corresponding Application).
Amendment and Reply to Office Action submitted Jun. 29, 2012, in U.S. Appl. No. 12/090,676, inventor: Kobara, M., filed Oct. 20, 2006, U.S. Patent and Trademark Office, Alexandria, VA.
Campochiaro, P.A., "Retinal and Choroidal Neovascularization," *J Cell. Physiol.* 184:301-310, Wiley-Liss, Inc. (2000).
Chuntharapai, A. and Kim, K.J., "Generation of Monoclonal Antibodies to Chemokine Receptors," *Meth. Enzymol.* 288:15-27, Academic Press (1997).
Fujita, J. et al., "Anti-Interleukin-6 Receptor Antibody Prevents Muscle Atrophy in Colon-26 Adenocarcinoma-Bearing Mice with Modulation of Lysosomal and ATP-Ubiquitin-Dependent Proteolytic Pathways," *Int. J. Cancer* 68:637-643, Wiley-Liss, Inc. (1996).
Greenberg, A.S, et al., "Interleukin 6 Reduces Lipoprotein Lipase Activity in Adipose Tissue of Mice in Vivo and in 3T3-L1 Adipocytes: A Possible Role for Interleukin 6 in Cancer Cachexia," *Canc. Res.* 52:4113-4116, American Association for Cancer Research (1992).
Nishimoto, N. et al., "Anti-interleukin 6 receptor antibody treatment in rheumatic disease," *Ann. Rheum. Dis.* 59(suppl I);i21-i27. BMJ Group (2000).
Ohtsuka, T. el al., "Relation of Circulating Interleukin-6 to Left Ventricular Remodeling in Patients with Reperfused Anterior Myocardial Infarction," *Clin. Cardiol.* 27:417-420, John Wiley & Sons, Inc. (2004).
Ono, M. et al., "The effect of IL-6 on the des-gamma-carboxy prothrombin synthesis in human hepatoma cells," *Gastroenterologia Japonica* 27:745-750, The Japanese Society of Gastroenterology (1992).
Puhakka, M. et al., "Interleukin-6 and Tumor Necrosis Factor Alpha in Relation to Myocardial Infarct Size and Collagen Formation," *J. Cardiac Failure* 9:325-332, Elsevier Inc. (2003).
Q&A de wakaru himan to tounyoubyou 3:982-984 (2004), with unverified English language translation.
Sato, K. et al., "Reshaping a Human Antibody to Inhibit the Interleukin 6-dependent Tumor Cell Growth," *Canc. Res.* 53:851-856, American Association for Cancer Research (1993).
Strassman, G. et al., "Evidence for the Involvement of Interleukin 6 in Experimental Cancer Cachexia," *J. Clin. Invest.* 89:1681-1684, The American Society for Clinical Investigation, Inc. (1992).
Amendment and Reply to Office Action submitted Jun. 20, 2012, in U.S. Appl. No. 12/524,041, inventors: Takahashi, M., et al., filed Jan. 23, 2008, U.S. Patent and Trademark Office, Alexandria, VA.
Office Action dated Oct. 15, 2012, in U.S. Appl. No. 12/524,041, inventors: Takahashi, M., et al., filed Jan. 23, 2008, U.S. Patent and Trademark Office, Alexandria, VA.

Amendment and Reply to Office Action submitted Jan. 15, 2013, in U.S. Appl. No. 12/524,041, inventor: Takahashi, M., et al., filed Jan. 23, 2008, U.S. Patent and Trademark Office, Alexandria, VA.
Akira, S. et al., "Interleukin-6 in Biology and Medicine," *Advances in Immunology* 54:1-78, Academic Press, Inc., San Diego, CA, USA (1993).
Unverified English language translation of French Patent No. FR 2 694 767 A1, published Feb. 18, 1994 (12 pages).
Furukawa, Y. et al., "Cytokine Gene Expression During the Development of Graft Coronary Artery Disease in Mice," *Japanese Circulation Journal* 63:775-782 Japanese Circulation Society, Kyoto, Japan (1999).
Hirano, T. el al., "Complementary DNA for a novel human interleukin (BSF-2) that induces B lymphocytes to produce immunoglobulin," *Nature* 324:73-76, Nature Publishing, London, UK (1986).
Hirata, Y. et al., "Characterization of IL-6 Receptor Expression by Monoclonal and Polyclonal Antibodies," *The Journal of Immunology* 143:2900-2906, The American Association of Immunologists (1989).
Hornick, P. et al., "Chronic Rejection in the Heart," *Methods in Molecular Biology* 333:131-144, Humana Press Inc,. Torowa, NJ, USA (2006).
Huang, Y.-W. et al., "A Monoclonal Anti-Human IL-6 Receptor Antibody Inhibits the Proliferation of Human Myeloma Cells," *Hybridoma* 12:621-630, Mary Ann Liebert, Inc., Larchmont, NY, USA (1993).
International Search Report for International Application No. PCT/JP2008/050842, Japanese Patent Office, Japan, dated Feb. 19, 2008 (2 pages) (Not a Corresponding Application).
Izawa, A. et al., "Critical Role of Interleukin-6 and its Crosstalk with AT1R Signaling in Acute Rejection of Murine Cardiac Allografts," *Circulation Journal* 71 (Suppl. 1):392 (#PE-269), Annual Scientific Meeting of the Japanese Circulation Society, Kobe, Japan (2007).
Izawa, A. et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," *American Journal of Transplantation* 7(Suppl 11):426(#1084), American Transplant Congress, San Francisco, CA, USA (2007).
Lotz, M. et al., "B cell Stimulating Factor 2/Interleukin 6 is a Costimulant for Human Thymocytes and T Lymphocytes," *The Journal of Experimental Medicine* 167:1253-1258, Rockefeller University Press, New York, NY, USA (1988).
Novick, D. et al., "Monoclonal Antibodies to the Soluble Human IL-6 Receptor: Affinity Purification, ELISA, and Inhibition of Ligand Binding," *Hybridoma* 10:137-146, Mary Ann Liebert, Inc., Larchmont, NY, USA (1991).
Ramzy, D. et al., "Cardiac allograft vasculopathy : a review," *Canadian Journal of Surgery* 48:319-327, Canadian Medical Association, Ottawa, ON, Canada (2005).
Taga, T. et al., "Receptors for B Cell Stimulatory Factor 2: Quantitation, Specificity, Distribution, and Regulation of Their Expression" *The Journal of Experimental Medicine* 166:967-981, Rockefeller University Press, New York, NY, USA (1987).
Taga, T. et al., "Interleukin-6 Triggers the Association of its Receptor with a Possible Signal Transducer, gp130," *Cell* 58:573-581, Cell Press, Cambridge, MA, USA (1989).
Valantine, H., "Cardiac Allograft Vasculopathy After Heart Transplantation: Risk Factors and Management," *The Journal of Heart and Lung Transplantation* 23:S187-S193, Elsevier Science, New York, NY, USA (2004).
Webber, S.A. et al., "Heart and lung transplantation in children," *Lancet* 368:53-69, Lancet, London, UK (2006).
Wong, B.W. et al., "Progress in heart transplantation," *Cardiovascular Pathology* 14:176-180, Elsevier Science, New York, NY, USA (2005).
Yamasaki, K. et al., "Cloning and Expression of the Human Interleukin-6 (BSF-2/IFNβ 2) Receptor," *Science* 241:825-828, American Association for the Advancement of Science, Washington, DC (1988).
Espacenet, European Patent Office, English language abstract of Japanese Patent Application Publication No. JP 2005-281235 A, published Oct. 13, 2005.

(56) References Cited

OTHER PUBLICATIONS

English language abstract of Furukawa, Y. et al., "Cytokine Gene Expression During the Development of Graft Coronary Artery Disease in Mice," *Japanese Circulation Journal* 63:775-782, Japanese Circulation Society, Kyoto, Japan (1999).
Bellomo, R., "The Cytokine Network in the Critically Ill," *Anaesth. Intensive Care* 20(3):288-302, Australian Society of Anaesthetists, Australia (Aug. 1992).
Benda, B. and Korsgren, O., "Interleukin-6 in Islet Xenograft Rejection," *Transplant Int.* 14:63-71, Springer-Verlag, Germany (2001).
Biswas, P.S., et al., "Involvement of IL-6 in the Paracrine Production of VEGF in Ocular HSV-1 Infection," *Exp. Eye Res.* 82:46-54, Elsevier Ltd., England (2006).
Borsellino, N., et al., "Blocking Signaling Through the Gp130 Receptor Chain by Interleukin-6 and Oncostatin M Inhibits PC-3 Cell Growth and Sensitizes the Tumor Cells to Etoposide and Cisplatin-Mediated Cytotoxicity," *Cancer* 85:134-144, American Cancer Society, USA (1999).
Campbell, I.L., et al., "Essential Role for Interferon-γ and Interleukin-6 in Autoimmune Insulin-Dependent Diabetes in NOD/Wehi Mice," *J. Clin. Invest.* 87;739-742, The American Society for Clinical Investigation, Inc., USA (Feb. 1991).
Campbell, I.L., et al., "Evidence for IL-6 Production by and Effects on the Pancreatic β-Cell," *J. Immunol.* 143(4):1188-1191, The American Society of Immunologists, USA (Aug. 1989).
Choi, S-E., et al., "IL-6 Protects Pancreatic Islet Beta Cells from Pro-Inflammatory Cytokines-Induced Cell Death and Functional Impairment in vitro and in vivo," *Transpl. Immunol.* 13:43-53, Elsevier B.V., The Netherlands (2004).
Culig, Z., et al., "Interleukin-6 Regulates Androgen Receptor Activity and Prostate Cancer Cell Growth," *Mol. Cell. Endocrinol.* 197:231-238, Elsevier Science Ireland Ltd., Ireland (2002).
Davies, G., et al., "The HGF/SF Antagonist NK4 Reverses Fibroblast- and HGF-Induced Prostate Tumor Growth and Angiogenesis In Vivo," *Int. J. Cancer* 106:348-354, Wiley-Liss, Inc., USA (2003).
Ding, W., et al., "The Change of Plasma Interleukin-6 Level and Cardiac Protective Effect of Monoclonal Antibody to IL-6 During Myocardial Infarction Reperfusion," *Chin. J. Cardiol.* 27(1):29-32, Chinese Medical Association Publishing House (Feb. 1991) (with English Abstract).
Eder, I.E., et al., "Targeting the Androgen Receptor in Hormone-Refractory Prostate Cancer—New Concepts," *Future Oncol.* 1(1):93-101, Future Medicine Ltd, England (2005).
Finkel, M.S., et al., "Negative Inotropic Effects of Cytokines on the Heart Mediated by Nitric Oxide," *Science* 257:387-389, American Association for the Advancement of Science, USA (Jul. 1992).
Ford, H.R., et al., "Evidence that Production on Interleukin 6 Within the Rejecting Allograft Coincides with Cytotoxic T Lymphocyte Development," *Transplantation* 51(3):656-661, Williams & Wilkins, USA (Mar. 1991).
Fuchs, M., et al., "Role of Interleukin-6 for LV Remodeling and Survival After Experimental Myocardial Infarction," *FASEB J* 17(14):2118-2120, The Federation of American Societies for Experimental Biology, USA (Nov. 2003).
Giugliano, G., et al., "Verapamil Inhibits Interleukin-6 and Vascular Endothelial Growth Factor Production in Primary Cultures of Keloid Fibroblasts," *Br. Assoc. Plast. Surg.* 56:804-809, Elsevier Ltd, England (2003).
Grossniklaus, H.E. and Green, R., "Choroidal Neovascularization," *Am. J. Ophthalmol.* 137:496-503, Elsevier Inc., USA (2004).
Gwechenberger, M. et al., "Cardiac Myocytes Product Interleukin-6 in Culture and in Viable Border Zone of Reperfused Infarctions," *Circulation* 99(4):546-551, American Heart Association, Inc., USA (1999).
Hirota, H., et al., "Continuous Activation of gp130, a Signal-Transducing Receptor Component for Interleukin 6-Related Cytokines, Causes Myocardial Hypertrophy in Mice," *Proc. Natl. Acad. Sci.* 92:4862-4866, The National Academy of Sciences, USA (May 1995).

Hoffman, S., et al., "Inhibitory Effects of Verapamil Isomers on the Proliferation of Choroidal Endothelial Cells," *Graefe's Arch. Clin. Exp. Ophthalmol.* 244:376-381, Springer-Verlag, Germany (2006).
Horinaga, M., et al., "Clinical and Pathologic Significance of Activation of Signal Transducer and Activator of Transcription 3 in Prostate Cancer," *Urology* 66:671-675, Elsevier Inc., USA (2005).
Ito, et al., "Regulation of Damage to Islets Transplanted into the Liver by IL-6 Receptor Antibody," *J. Japan Surg. Soc. 107* (*special extra issue 2*):387(#PS-014-5), 2006 (English Translation) (Abstract Only).
Itoh, T., et al., "Anti-IL-6 Receptor Antibody Down-Regulates Pro-Inflammatory Cytokine Production of Gr-1 *CD11b* Cells and Prevents Early Loss of Islet Grafts in the Liver of Mice in Association with Engraftments," *Transplantation* 82(Supp.3):Abstract No. 2838, World Transplant Congress (2006)(Abstract Only).
Jeron, A., et al., "Systemic Immunosuppression Fails to Suppress Cardiac Cytokine Induction in Pressure Overload Hypertrophy in Rats," *Immunobiol.* 205:51-60, Urban & Fischer Verlag, Germany (2002).
Kallen, K-J., et al., "New Developments in IL-6 Dependent Biology and Therapy: Where Do We Stand and What are the Options?," *Exp. Opin. Invest. Drugs* 8(9):1327-1349, Ashley Publications Ltd., England (1999).
Kobara, M., et al., "Inhibition of Interleukin-6 Signaling Attenuates Left Ventricular Remodeling After Myocardial Infarction in Mice," *Circulation Supplement II* 112(17):Abstract 851, The American Heart Association, USA (Oct. 2005) (Abstract Only).
Kurdi, M., et al., "Increased Expression of IL-6 and LIF in the Hypertrophied Left Ventricle of TGR(mRen2)27 and SHR Rats," *Mol. Cell. Biochem.* 269:95-101, Springer, The Netherlands (2005).
Kuroda, K., et al., "Prevention of Cancer Cachexia by a Novel Nuclear Factor κB inhibitor in Prostate Cancer," *Clin. Cancer Res.* 11(15):5590-5594, American Association for Cancer Research, USA (Aug. 2005).
Lee, S.O., et al., "Interleukin-6 Protects LNCaP Cells from Apoptosis Induced by Androgen Deprivation Through the Stat3 Pathway," *The Prostate* 60:178-186, Wiley-Liss, Inc., USA (2004).
Luo, H., et al., "A Proteasome Inhibitor Effectively Prevents Mouse Heart Allograft Rejection," *Transplantation* 72(2):196-202, Lippincott Williams & Wilkins, Inc., USA (Jul. 2001).
Nagai, et al., "Suppression of Experimental Choroid Neovascularization by Inhibition of Interleukin-6 Receptor," *Inflammation and Regeneration* 26(4):367 (#90), The Japanese Society of Inflammation and Regeneration, Japan (Jul. 2006) (English Translation) (Abstract Only).
Nakashima, J., et al., "Serum Interleukin 6 as a Prognostic Factor in Patients with Prostate Cancer," *Clin. Cancer Res.* 6:2702-2706, American Association for Cancer Research, USA (Jul. 2000).
Negoro, S., et al., "Activation of JAK/STAT Pathway Transduces Cytoprotective Signal in Rat Acute Myocardial Infarction," *Cardiovas. Res.* 47:797-805, Elsevier Science B.V., The Netherlands (2000).
Nishimoto, N. and Kishimoto, T., "Inhibition of IL-6 for the Treatment of Inflammatory Diseases," *Curr. Opin. Pharmacol.* 4:386-391, Elsevier Ltd., England (2004).
Okamoto, M., et al., "Interleukin-6 as a Paracrine and Autocrine Growth Factor in Human Prostatic Carcinoma Cells in Vitro," *Cancer Res.* 57:141-146, American Association for Cancer Research, USA (Jan. 1997).
Okamoto, A. et al., "Inhibition of Interleukin-6 Signaling Attenuates Left Ventricular Remodeling After Experimental Myocardial Infarction," *J. Heart Failure Supplement* 11:P-066, Heart Failure Society of America, USA (2005)(Abstract Only).
Okazaki, M. et al., "Characterization of Anti-Mouse Interleukin-6 Receptor Antibody," *Immunol. Lett.* 84:231-240, Elsevier Science B.V., The Netherlands (2002).
Ono, K., et al., "Cytokine Gene Expression After Myocardial Infarction in Rat Hearts," *Circulation* 98:149-156, American Heart Association, USA (1998).
Park, H., et al., "Interleukin-6 Protects MIN6 β Cells from Cytokine-Induced Apoptosis," *Ann. N.Y. Acad, Sci.* 1005:242-249, New York Academy of Sciences, USA(2003).

(56) References Cited

OTHER PUBLICATIONS

Paul, W.E., "Transplantation and Graft Rejection," in *Fundamental Immunology*, Third Edition, pp. 1124-1125, Raven Press, Ltd., USA (1993).
Paule, B., "Reappraisal of the Concept of Hormone Therapy in Metastatic Prostate Cancer and Implications for Treatment," *Eur. Urol.* 47:729-735, Elsevier B.V., The Netherlands (2005).
Pauleikhoff, D., "Neovascular Age-Related Macular Degeneration," *Retina* 25:1065-1084, Lippincott Williams & Wilkins, USA (2005).
Seddon, J.M., et al., "Progression of Age-Related Macular Degeneration," *Arch. Ophthalmol.* 123:774-782, American Medical Association, USA(Jun. 2005).
Shimazaki, et al., "Human Myeloma Model and Antitumor Effect of Anti-Human IL-6 Receptor Antibody," *Rinsho Ketsueki*. 38(4):281-284,The Japanese Society of Hematology, Japan (Apr. 1997) (English Translation).
Smith, P.C. and Keller, E.T., "Anti-Interleukin-6 Monoclonal Antibody Induces Regression of Human Prostate Cancer Xenografts in Nude Mice," *The Prostate* 48:47-53, Wiley-Liss, Inc., USA (2001).
Smith, T.F. and Zhang, X., "The Challenges of Genome Sequence Annotation or 'The Devil is in the Details'," *Nat. Biotechnol.* 15:1222-1223, Nature Publishing Group, USA (1997).
Trikha, M., et al., "Targeted Anti-Interleukin-8 Monoclonal Antibody Therapy for Cancer: A Review of the Rationale and Clinical Evidence," *Clin. Cancer Res.* 9:4653-4665, American Association for Cancer Research, USA (Oct. 2003).
Xing, Y., et al., "The Effect of Interleukin-6 on the Proliferation of Prostate Cancer Cells in Vitro and the Modulation of This Procedure," *J. Tongji Med. Univ.* 21(3):225-227, Springer-Verlag, Germany (2001).
Yamauchi-Takihara, K., et al., "Hypoxic Stress Induces Cardiac Myocyte-Derived Interleukin-6," *Circulation* 91:1520-1524, The American Heart Association, USA (1995).
Yue, P., et al. "Cytokine Expression Increases in Nonmyocytes from Rats with Postinfarction Heart Failure," *Am. J. Physiol.* 275:H250-H258, American Physiological Society, USA (1998).
Zaki, M.H., et al, "CNTO 328, A Monoclonal Antibody to IL-6, Inhibits Human Tumor-Induced Cachexia in Nude Mice," *Int. J. Cancer* 111:592-595, Wiley-Liss, Inc., USA (2004).
Response to Restriction Requirement filed on Oct. 22, 2010, in U.S. Appl. No, 12/085,065, inventors Okada, M., et al., filed Nov. 15, 2006, U.S. Patent and Trademark Office, Alexandria, VA.
Office Action dated Nov. 26, 2010, in U.S. Appl. No. 12/085,065, inventors Okada, M., et al., filed Nov. 15, 2006, U.S. Patent and Trademark Office, Alexandria, VA.
Amendment and Reply to Office Action filed on May 25, 2011, in U.S. Appl. No. 12/085,065, inventors Okada, M., et al., filed Nov. 15, 2006, U.S. Patent and Trademark Office, Alexandria, VA.
Response to Restriction Requirement filed Feb. 24, 2011, in U.S. Appl. No. 12/090,061, inventor Yasunami, Y., filed Oct. 13, 2006, U.S. Patent and Trademark Office, Alexandria.
Office Action dated May 3, 2011, in U.S. Appl. No. 12/090,061, inventor Yasunami, Y., filed Oct. 13, 2006, U.S. Patent and Trademark Office, Alexandria.
Amendment and Reply to Office Action filed on Apr. 5, 2011, in U.S. Appl. No. 12/090,676, inventors Kobara, M., filed Oct. 20, 2006, U.S. Patent and Trademark Office, Alexandria, VA.
Office Action dated Jun. 8, 2011, in U.S. Appl. No. 12/090,676, inventors Kobara, M., et al., filed Oct. 20, 2006, U.S. Patent and Trademark Office, Alexandria, VA.
Office Action dated Feb. 2, 2011, in U.S. Appl. No. 12/094,644, inventors Nakashima, J., et al., filed Nov. 24, 2006, U.S. Patent and Trademark Office, Alexandria, VA.
Response to Restriction Requirement filed Jul. 25, 2011, in U.S. Appl. No. 12/094,644, inventors Nakashima, J., et al., filed Nov. 24, 2006, U.S. Patent and Trademark Office, Alexandria, VA.
Office Action dated Jan. 13, 2011, in U.S. Appl. No. 12/161,733, inventor Ishida, S., filed Jan. 26, 2007, U.S. Patent and Trademark Office, Alexandria, VA.
Response to Restriction Requirement filed Jul. 7, 2011, in U.S. Appl. No. 12/161,733, inventor Ishida, S., filed Jan. 26, 2007, U.S. Patent and Trademark Office, Alexandria, VA.
Response to Restriction Requirement filed on Nov. 2, 2010, in U.S. Appl. No. 12/296,193, inventors Nishimoto, N., et al., filed Apr. 6, 2007, U.S. Patent and Trademark Office, Alexandria, VA.
Office Action dated Dec. 20, 2010, in U.S. Appl. No. 12/296,193, inventors Nishimoto, N., et al., dated Apr. 6, 2007, U.S. Patent and Trademark Office, Alexandria, VA.
Amendment and Reply to Office Action filed on Jun. 20, 2011, in U.S. Appl. No. 12/296,193, inventors Nishimoto, N., et al., filed Apr. 6, 2007, U.S. Patent and Trademark Office, Alexandria, VA.
Office Action dated Jul. 26, 2011, in U.S. Appl. No. 12/296,193, inventors Nishimoto, N., et al., filed Apr. 6, 2007, U.S. Patent and Trademark Office, Alexandria, VA.
Extended European Search Report in European Patent Appl. No. 06 811 729.0, Applicants Fukuoka University, et al., dated Dec. 23, 2009, European Patent Office, The Netherlands (Not a Corresponding Application).
Extended European Search Report in European Patent Appl. No. 06 832 657.8, Applicants National Hospital Organization, et al., dated Dec. 3, 2009, European Patent Office, The Netherlands (Not a Corresponding Application).
Extended European Search Report in European Patent Appl. No. 06 812 073.2, Applicant Chugai Seiyaku Kabushiki Kaisha, dated Dec. 7, 2009, European Patent Office, The Netherlands (Not a Corresponding Application).
Extended European Search Report in European Patent Appl. No. 06 833 196.6, Applicant Keio University, et al., dated Sep. 8, 2009, European Patent Office, The Netherlands (Not a Corresponding Application).
Extended European Search Report in European Patent Appl. No. 07 707 458.1, Applicant Keio University, et al., dated Dec. 11, 2009, European Patent Office, The Netherlands (Not a Corresponding Application).
Extended European Search Report in European Patent Appl. No. 07 741 181.7, Applicant Osaka University, et al., dated Dec. 23, 2009, European Patent Office, The Netherlands (Not a Corresponding Application).
International Search Report for International Application No. PCT/JP2006/320441, dated Dec. 19, 2006, Japanese Patent Office, Japan (Not a Corresponding Application).
International Preliminary Report on Patentability with Written Opinion of the International Searching Authority for International Application No. PCT/JP2006/320441, dated Apr. 16, 2008, The International Bureau of WIPO, Switzerland (Not a Corresponding Application).
International Search Report for International Application No. PCT/JP2006/322726, dated Jan. 9, 2007, Japanese Patent Office, Japan (Not a Corresponding Application).
International Preliminary Report on Patentability with Written Opinion of the International Searching Authority for International Application No. PCT/JP2006/322726, dated May 20, 2008, The International Bureau of WIPO, Switzerland (Not a Corresponding Application).
International Search Report for International Application No. PCT/JP2006/320905, dated Jan. 16, 2007, Japanese Patent Office, Japan (Not a Corresponding Application).
International Preliminary Report on Patentability with Written Opinion of the International Searching Authority for International Application No. PCT/JP2006/320905, dated Apr. 22, 2008, The International Bureau of WIPO, Switzerland (Not a Corresponding Application).
International Search Report for International Application No. PCT/JP2006/323392, dated Jan. 9, 2007, Japanese Patent Office, Japan (Not a Corresponding Application).
International Preliminary Report on Patentability with Written Opinion of the International Searching Authority for International Application No. PCT/JP2006/323392, dated May 27, 2008, The International Bureau of WIPO, Switzerland (Not a Corresponding Application).
International Search Report for International Application No. PCT/JP2007/051226, dated May 1, 2007, Japanese Patent Office, Japan (Not a Corresponding Application).
International Preliminary Report on Patentability with Written Opinion of the International Searching Authority for International Appli-

(56) References Cited

OTHER PUBLICATIONS cation No. PCT/JP2007/051226, dated Jul. 29, 2008, The International Bureau of WIPO, Switzerland (Not a Corresponding Application).
International Search Report for International Application No. PCT/JP2007/057745, dated Jul. 10, 2007, Japanese Patent Office, Japan (Not a Corresponding Application).
International Preliminary Report on Patentability with Written Opinion of the International Searching Authority for International Application No. PCT/JP2007/057745, dated Nov. 17, 2008, The International Bureau of WIPO, Switzerland (Not a Corresponding Application).
International Search Report for International Application No. PCT/JP2009/060314, dated Aug. 11, 2009, Japanese Patent Office, Japan.
International Preliminary Report on Patentability with Written Opinion of the International Searching Authority for International Application No. PCT/JP2009/060314, dated Jan. 11, 2011, The International Bureau of WIPO, Switzerland.
English language Abstract of Russian Patent Publication No. RU 2 127 117 C1, published Mar. 10, 1993, European Patent Office, Espacenet, Worldwide Database.
Huang, C., et al., "Inhibitory effect of AG490 on invasion and metastasis of human pancreatic cancer cells in vitro," *Chin. J. Oncol.* 28:890-893, Wanfang Data Co., Beijing, China (2006).
Huang, C., et al., "Inhibition of STAT3 activity with AG490 decreases the invasion of human pancreatic cancer cell in vitro," *Cancer Science* 97:1417-1423, Japanese Cancer Association, Tokyo, Japan (2006).
Nishimoto, N., "Clinical Studies in Patients With Castleman's Disease, Crohn's Disease, and Rheumatoid Arthritis in Japan," *Clinical Reviews in Allergy & Immunology* 28:221-230, Humana Press, United States (2005).
Ogata, T. et al., "Early administration of IL-6RA does not prevent radiation-induced lung injury in mice," *Radiation Oncology* 5:26, BioMed Central, London (2010).
Ogata, T. et al., "Anti-IL-6 receptor antibody does not ameliorate radiation pneumonia in mice," *Exp. Ther. Med.* 4:273-276, Spandidos Publications, Greece (2012).
Y. Ohsugi and N. Tsuchimoto, Pharmacological and Clinical Profile of Humanized Anti-human IL-6 Receptor Anibody (Tocilizumab), a Therapeutic Drug for Castleman's Disease, *Folia Pharmacol. Jpn.* 126:419-425, Japan (2005).
Unverified English language translation of Y. Ohsugi and N. Tsuchimoto, Pharmacological and Clinical Profile of Humanized Anti-human IL-6 Receptor Anibody (Tocilizumab), a Therapeutic Drug for Castleman's Disease, *Folia Pharmacol. Jpn.* 126:419-425, Japan (2005).
Okada, S., et al., "Elevated Serum Interleukin-6 Levels in Patients with Pancreatic Cancer," *Japanese Journal of Clinical Oncology* 28:12-15, Foundation of Clinical Oncology, Tokyo, Japan (1998).
Roitt, I., et al., "Immunology," Fifth Edition, 110, Mir, Moscow, Russia (2000).
Unverified English translation of: Roitt, I., et al., "Immunology," Fifth Edition, 110, Mir, Moscow, Russia (2000).
Rudikoff, S., et al., "Single amino acid substitution altering antigen binding specificity," *Proc. Natl. Acad. Sci. USA* 79:1979-1983, United States (1982).
Yokota, S., et al., "Clinical Study of Tocilizumab in Children With Systemic-Onset Juvenile Idiopathic Arthritis," *Clinical Reviews in Allergy & Immunology* 28:231-238, Humana Press, United States (2005).
International Preliminary Report on Patentability for International Patent Application No. PCT/JP2010/062874, The International Bureau of WIPO, Geneva, Switzerland, dated Feb. 7, 2012 (Not a Corresponding Application).
Amendment and Reply filed Jul. 11, 2013, in U.S. Appl. No. 12/085,065, § 371(c) date of Jun. 1, 2009, inventors: Okada, M., et al., U.S. Patent and Trademark Office, Alexandria, VA.
Notice of Allowance dated Mar. 22, 2013, for U.S. Appl. No. 12/090,061, inventor Yasunami, Y., filed Oct. 13, 2006, U.S. Patent and Trademark Office, Alexandria, VA.

Office Action dated Mar. 15, 2013, in U.S. Appl. No. 12/524,041, inventors: Takahashi, M., et al., filed Jan. 23, 2008, U.S. Patent and Trademark Office, Alexandria, VA.
Reply to Office Action filed on Sep. 13, 2013, in U.S. Appl. No. 12/524,041, inventors: Takahashi, M., et al., filed Jan. 23, 2008, U.S. Patent and Trademark Office, Alexandria, VA.
Restriction Requirement in U.S. Appl. No. 13/387,292, Maeda., filed Jul. 30, 2010, dated Jan. 31, 2013, U.S. Patent and Trademark Office, Alexandria, VA.
Response to Restriction Requirement filed on Mar. 1, 2013, in U.S. Appl. No. 13/387,292, inventors Maeda, S., et al., filed Jul. 30, 2010, U.S. Patent and Trademark Office, Alexandria, VA.
Office Action dated Mar. 26, 2013, in U.S. Appl. No. 13/387,292, inventor Maeda, filed Jul. 30, 2010, U.S. Patent and Trademark Office, Alexandria, VA.
Hanahan, D. and Weinberg, R.A., "Hallmarks of Cancer: The Next Generation," *Cell* 144:646-674, Elsevier, Inc. (2011).
Tsuchiya, M., "Therapeutic Antibody," Credit Suisse Seminar at Fuji-Gotemba Research Laboratories, p. 21, Shizuoka, Japan (2006).
Unverified English translation of Tsuchiya, M., "Therapeutic Antibody," Credit Suisse Seminar at Fuji-Gotemba Research Laboratories, p. 21, Shizuoka, Japan (2006).
Akira, S., et al., "The evidence for interleukin-6 as an autocrine growth factor in malignancy," *Cancer Biology* 3:17-26 (1992).
Armstrong, C.A., et al., "Melanoma-Derived Interleukin 6 Inhibits In Vivo Melanoma Growth," *Journal of Investigative Dermatology* 102:278-284 (1994).
Becker, Y., "Molecular Immunological Approaches to Biotherapy of Human Cancers—A Review, Hypothesis, and Implications," *Anticancer Research* 26:1113-1134 (2006).
Cabillic, F., et al., "Interleukin-6 and vascular endothelial growth factor release by renal cell carcinoma cells impedes lymphocyte-dendritic cell cross-talk," *Clinical and Experimental Immunology* 146:518-523 (2006).
Duluc, D., et al., "Tumor-associated leukemia inhibitory factor and IL-6 skew monocyte differentiation into tumor-associated macrophage-like cells," *Blood* 110(13):4319-4330 (2007).
Porgador, A., et al., "Interleukin 6 Gene Transfection into Lewis Lung Carcinoma Tumor Cells Suppresses the Malignant Phenotype and Confers Immunotherapeutic Competence against Parental Metastatic Cells," *Cancer Research* 52:3679-3686 (1992).
Sebba, A., "Tocilizumab: The first interleukin-6-receptor inhibitor," *American Journal of Health-System Pharmacy* 65:1413-1418 (2008).
Suzuki, E., et al., "Gemcitabine Selectively Eliminates Splenic Gr-1$^+$/CD11b$^+$ Myeloid Suppressor Cells in Tumor-Bearing Animals and Enhances Antitumor Immune Activity," *Clinical Cancer Research* 11(18):6713-6721 (2005).
Tanaka, F., et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," *Cancer Research* 57:1335-1343 (1997).
Vincent, J., et al., "5-Fluorouracil Selectively Kills Tumor-Associated Myeloid-Derived Suppressor Cells Resulting in Enhanced T Cell-Dependent Antitumor Immunity," *Cancer Research* 70(8):3052-3061(2010).
Zangari, M., et al., "Immunomodulatory drugs in multiple myeloma," *Expert Opinion on Investigative Drugs* 14(11):1411-1418 (2005).
Berger, T. et al., "Disruption of the Lcn2 gene in mice suppresses primary mammary tumor formation but does not decrease lung metastasis," *Proc. Natl. Acad. Sci.* 107(7):2995-3000 (2010).
Kim, S. et al., "Carcinoma-produced factors activate myeloid cells through TLR2 to stimulate metastasis," *Nature* 457:102-106 (2009).
Shewach, D.S. et al., "Gemcitabine and radiosensitization in human tumor cells," *Investigational New Drugs* 14:257-263 (1996).
Yoshio-Hoshino, N. et al., "Establishment of a New Interleukin-6 (IL-6) Receptor Inhibitor Applicable to the Gene Therapy for IL-6-Dependent Tumor," *Cancer Res.* 67:871-875, American Association for Cancer Research (2007).
Chung, Y.-C. and Chang, Y.-F., "Serum Interleukin-6 Levels Reflect the Disease Status of Colorectal Cancer," *J. Surg. Oncol.* 83:222-226, Wiley-Liss, Inc. (2003).

(56) References Cited

OTHER PUBLICATIONS

Michalaki, V., et al., "Serum levels of IL-6 and TNF-α correlate with clinicopathoological features and patient survival in patients with prostate cancer," *Br. J. Cancer* 90:2312-2316, Cancer Research UK (2004).

Mitsunaga, S., et al., "Detail Histologic Analysis of Nerve Plexus Invasion in Invasive Ductal Carcinoma of the Pancreas and Its Prognostic Impact," *Am. J. Surg. Pathol.* 31:1636-1644, Lippincott Williams & Wilkins (2007).

Mitsunaga, S., et al., "Nerve invasion distance is dependent on laminin γ2 in tumors of pancreatic cancer," *Int. J. Cancer* 127:805-819, UICC (2010).

Zhang, G.-J. and Adachi, I., "Serum Interleukin-6 Levels Correlate to Tumor Progression and Prognosis in Metastatic Breast Carcinoma," *Anticancer Res.* 19:1427-1432, International Institute of Anticancer Research, Attiki, Greece (1999).

Hatzi, E., et al., "N-myc oncogene overexpression down-regulates IL-6; evidence that IL-6 inhibits angiogenesis and suppresses neuroblastoma tumor growth," *Oncogene* 21:3552-3561, Nature Publishing Group, England (2002).

Jones, S.W., et al., "Disuse atrophy and exercise rehabilitation in humans profoundly affects the expression of genes associated with the regulation of skeletal muscle mass," *FASEB Journal* 18(9):1025-1027, Federation of American Societies for Experimental Biology, United States (2004).

Konopatskaya, O., et al., "VEGF165b, an Endogenous C-Terminal Splice Variant of VEGF, Inhibits Retinal Neovascularisation in Mice," *Invest. Ophthalmol. Vis. Sci.* 47:E-Abstract 1749-B836, Association for Research in Vision and Ophthalmology, Inc. (2006).

Fujiwara, et al., "Control of tumor immunity by B cells and Th2 cytokines," *Annual Review Men'eki* 1999:257-269 (1999).

Kan, S., et al., "The effect of anti-cancer agents on CD4+FoxP3+ regulatory T cell," *Dai 68 Kai Annual Meeting of the Japan Cancer Association*, p. 286, P-0539 (2009).

Narita, et al., "Gemcitabine selectively depletes $CD11b^+$ $Gr-1^+$ immature myeloid cells in tumor-bearing mice and enhances anti-tumor immune response," *Society for Fundamental Cancer Immunology Sokai Shoroku* 10:49 (2006).

Yamamoto, N., et al., "Regulatory Mechanisms for Production of IFN-γ and TNF by Antitumor T Cells or Macrophages in the Tumor-Bearing State," *Journal of Immunology* 154(5):2281-2290, The American Association of Immunologists, United States (1995).

International Search Report for International Patent Application No. PCT/JP2011/062209, Japanese Patent Office, Japan, dated Jul. 12, 2011.

Unverified English language translation of Fujiwara, et al., "Control of tumor immunity by B cells and Th2 cytokines," *Annual Review Men'eki* 1999:257-269 (1999).

Unverified English language translation of Narita, et al., "Gemcitabine selectively depletes $CD11b^+$ $Gr-1^+$ immature myeloid cells in tumor-bearing mice and enhances anti-tumor immune response," *Society for Fundamental Cancer Immunology Sokai Shoroku* 10:49 (2006).

Unverified English language translation of TW 201021839 A1, published Jun. 16, 2010, in the name of Chugai Seiyaku Kabushiki Kaisha.

Ito, N., et al., "Induction of Interleukin-6 by Interferon Alfa and Its Abrogation by a Serine Protease Inhibitor in Patients With Chronic Hepatitis C," *Hepatology* 23(4):669-675, American Association for the Study of Liver Diseases, United States (1996).

Tantraworasin, A., et al., "Prognostic factors of tumor recurrence in completely resected non-small cell lung cancer," *Cancer Management and Research* 5:77-84, Dove Medical Press, United Kingdom (2013).

Hudes, G.R., et al., "Preliminary results of a phase I study: A chimeric monoclonal anti IL-6 antibody CNTO 328 in combination with docetaxel in patients with hormone refractory prostate cancer," *Journal of Clinical Oncology* 25(18S): 15521, American Society of Clinical Oncology, United States (2007) (Abstract for ASCO Annual Meeting).

Salgado, R., et al., "Circulating Interleukin-6 Predicts Survival in Patients With Metastatic Breast Cancer," *Int. J. Cancer* 103:642-646, Wiley-Liss, Inc., United States (2003).

Bertagnolli, M.M. et al. "IL-4-Supported Induction of Cytolytic T Lymphocytes Requires IL-2 and IL-6," *Cellular Immunology* 133:327-341, Academic Press, United States (1991).

Borg, A.J., et al., "15-Deoxyspergualin inhibits interleukin 6 production in in vitro stimulated human lymphocytes," *Transplant Immunology* 4:133-143, Elsevier, Netherlands (1996).

Bork, P. and Bairoch, A., "Go hunting in sequence databases but watch out for the traps," *Trends in Genetics* 12:425-427, Elsevier Science Ltd. United Kingdom (1996).

Charge, S.B.P. and Rudnicki, M.A., "Cellular and Molecular Regulation of Muscle Regeneration," *Physiology Reviews* 84:209-238, The American Physiological Society, United States (2004).

Fraunberger, P., et al., "Cytokine and Cytokine-Receptor Profiles After Liver and Heart Transplant," *Transplantation Proceedings* 27:2023-2027, Appleton & Lange, United States (1995).

Kanda, T. and Takahashi, T., "Interleukin-6 and Cardiovascular Diseases," *Japanese Heart Journal* 45:183-193, Japanese Heart Journal Association, Japan (2004).

Kitahara, M. et al., "The in vivo Anti-tumor Effect of Human Recombinant Interleukin-6," *Japanese Journal of Cancer Research* 81:1032-1038, Elsevier Science Publishers, Netherlands (1990).

Ming, J.E., et al., "IL-6 enhances the generation of cytolytic T lymphocytes in the allogeneic mixed leucocyte reaction," *Clinical Experimental Immunology* 89:148-153, Blackwell Scientific Publications, Netherlands (1992).

Okada, M., et al., "IL-6/BSF-2 Functions as a Killer Helper Factor in the In Vitro Induction of Cytotoxic T Cells," *The Journal of Immunology* 141:1543-1549, The American Association of Immunologists, United States (1988).

Snow, M.H., "Myogenic Cell Formation in Regenerating Rat Skeletal Muscle Injured by Mincing: I. A Fine Structural Study," *Anat. Rec.* 188:181-200, The Wistar Institute of Anatomy and Biology, United States (1977).

Weyand, M., et al., "Serial Interleukin-6 Blood Levels Early After Cardiac Transplantation," *Transplantation Proceedings* 24(6):2546, Appleton & Lange, United States (1992).

Yang, Y-F., et al., "Enhanced Induction of Antitumor T-Cell Responses by Cytotoxic T Lymphocyte-associated Molecule-4 Blockade: The Effect is Manifested Only at the Restricted Tumor-bearing Stages," *Cancer Research* 57:4036-4041, American Association for Cancer Research, United States (1997).

Kitazawa, R., et al., "Interleukin-1 Receptor Antagonist and Tumor Necrosis Factor Binding Protein Decrease Osteoclast Formation and Bone Resorption in Ovariectomized Mice," *J. Clin. Invest* 94:2397-2406, The American Society for Clinical Investigation, Inc., United States (1994).

Lancaster, J.M., et al., "Identification of genes associated with ovarian cancer metastasis using microarray expression analysis," *Int J Gynecol Cancer* 16:1733-1745, Lippincott Williams & Wilkins, United States (2006).

Latulippe, E., et al., "Comprehensive Gene Expression Analysis of Prostate Cancer Reveals Distinct Transcriptional Programs Associated with Metastatic Disease," *Cancer Research* 62:4499-4506, American Association for Cancer Research, United States (2002).

MedlinePlus, U.S. National Library of Medicine NIH National Institutes of Health, "Liver metastases,"www.nlm.nih.gov/medlineplus/ency/article/000277.htm, accessed Nov. 22, 2014.

National Cancer Institute, U.S. National Institutes of Health, "Metastatic Cancer: Questions and Answers," web.archive.org/web/20100110123630/http://www.cancer.gov/publications, accessed Nov. 22, 2014.

Poli, V., et al., "Interleukin-6 deficient mice are protected from bone loss caused by estrogen depletion," *The EMBO Journal* 13(5):1189-1196, Oxford University Press, United Kingdom (1994).

Sacchi, A., et al., "Treatment With Monoclonal Antibody to a Lewis Lung Carcinoma-Associated Antigen: Different Effects on Primary Tumor and Its Metastases," *Cancer Treatment Reports* 69(9):985-991, Oxford University Press, United Kingdom (1985).

Japan Platform for Patent Information, unverified English language machine translation of JP 2008-297315 A, published Dec. 11, 2008.

(56) References Cited

OTHER PUBLICATIONS

Meng, F., et al., "Acquired Resistance to Chemotherapy in Human Cholangiocarcinoma is Mediated by an Interleukin (il-6) Dependent Activation of the X-Linked Inhibitor of Apoptosis (xiap) Protein," *Gastroenterology* 128(4):Supplemental 2:A-30, Abstract No. 165 (2005).
Meng, F., et al., "Over-expression of interleukin-6 enhances cell survival and transformed cell growth in human malignant cholangiocytes," *Journal of Hepatology* 44:1055-1065, Elsevier B.V., Netherlands (2006).
Ozaki, H., et al., "Effectiveness of Multimodality Treatment for Resectable Pancreatic Cancer," *International Journal of Pancreatology* 7:195-200, Humana Press, United States (1990).
Kayahara, M., et al., "Neural Invasion and Lymph Node Metastasis in the Head of the Pancreas Carcinoma," *The Japanese Journal of Gastroenterological Surgery* 24(3):813-817, The Japanese Society of Gastroenterological Surgery, Japan (1991).
Nakamura, T., "Cancer prevention by NK 4 to act as an inhibitor of tumor invasion, metastasis and angiogenesis," The Basics and Clinical Aspects of Angiogenesis—[II] Angiogenesis and Tumors, 8. Invasion/Metastasis/tumor Suppression of Angiogenesis-Inhibitory Factor AK 4, pp. 57-66, Japanese Association of Medical Sciences (2002).
Unverified English language translation of Nakamura, T., "Cancer prevention by NK 4 to act as an inhibitor of tumor invasion, metastasis and angiogenesis," The Basics and Clinical Aspects of Angiogenesis—[II] Angiogenesis and Tumors, 8. Invasion/Metastasis/tumor Suppression of Angiogenesis-Inhibitory Factor AK 4, pp. 57-66, Japanese Association of Medical Sciences (2002).
Yan, L., "(II) Abdominal discomfort and pain," *Theory and Practice of Oncology*, Shandong Science and Technology Press, 2 pages (2006).
Zijun, L., "Tissue Infiltration," *Tumor Metastasis*, Shanxi Science and Technology Press, 5 pages (2007).
Sugahara, H., et al., "Expression of Interleukin-6 in Human Intrahepatic Biliary Tract and its Pathologic Significance; An Immunohistochemical and In situ Hybridization Study," *J. Juzen Med. Soc.* 105:819-833, Japan (1996).
Araki, M., et al., "Efficacy of the anti-IL-6 receptor antibody tocilizumab in neuromyelitis optica," *Neurology* 82:1302-1306, American Academy of Neurology, Untied States (2014).
Barkhof, F., et al., "Comparison of MRI criteria at first presentation to predict conversion to clinically definite multiple sclerosis," *Brain* 120:2059-2069, Oxford University Press, England (1997).
Chihara, N., et al., "Interleukin 6 signaling promotes anti-aquaporin 4 autoantibody production from plasmablasts in neuromyelitis optica," *Proceedings of the National Academy of Sciences* 108(9):3701-3706, National Academy of Science, United States (2011).
Chihara, N., et al., "Autoantibody producing cells in neuromyelitis optica," *J. Clinical and Experimental Medicine* 240(6):534-535, Elsevier Taiwan, LLC (2012) (unverified English language translation included).
Christensen, J.R., et al., "Systemic Inflammation in Progressive Multiple Sclerosis Involves Follicular T-Helper, Th17- and Activated B-Cells and Correlates with Progression," *PLoS ONE* 8(3):e57820, 23 pages (2013).
Hosokawa, T., et al., "Evaluation of Interferon-β1b Treatment for Multiple Sclerosis," *Shinkei Chiryo* 25:589-595 (2008) (unverified English language translation included).
Houzen, H., et al., "Increased prevalence, incidence, and female predominance of multiple sclerosis in northern Japan," *Journal of the Neurological Sciences* 323:117-122, Elsevier, B.V., Netherlands (2012).
International Search Report for International Application No. PCT/JP2014/065449, Japanese Patent Office, Japan, dated Sep. 22, 2014, 2 pages.
Kakuron III "Section 9 Opticospinal Multiple Sclerosis," *Tahatsusei Kokasho Chiryo Guideline* 2010:104-109, Societas Neurologica Japonica (2010) (unverified English language translation included).

Lucchinetti, C., et al.., "Heterogeneity of Multiple Sclerosis Lesions: Implications for the Pathogenesis of Demyelination," *Annals of Neurology* 47:707-717, American Neurological Association, United States (2000).
Miller, D.H., et al., "Differential diagnosis of suspected multiple sclerosis: a consensus approach," *Multiple Sclerosis* 14:1157-1174, SAGE Publications, United States (2008).
Nakamura et al., "IL-6-dependent Plasmablasts in Pathological Conditions of Relapsing-Remitting Multiple Sclerosis," *Jap. J. Clin. Immunol.* 36:345, W5-5 (2013) (unverified English language translation included).
Nakamura, M., et al., "Clinical Features of Multiple Sclerosis with High Plasmablast Frequency in Peripheral Blood," Poster Session, 54th Annual Meeting of the Japanese Society of Neurology, Tokyo, Japan, presented Jun. 1, 2013.
Nakamura et al., "Clinical Characteristics of Multiple Sclerosis with High Peripheral Blood Plasmablast Frequency," Meeting Abstract, 54th Annual Meeting of the Japanese Society of Neurology, Tokyo, Japan, published Apr. 30, 2013 (unverified English language translation included).
Nakamura, M., et al., "Clinical features of multiple sclerosis with high plasmablast frequency in peripheral blood," Poster Session, Multiple Sclerosis, Keystone Symposia on Molecular and Cellular Biology, Big Sky, Montana, presented Jan. 14, 2013.
Nakamura, et al., "Clinical features of multiple sclerosis with high plasmablast frequency in peripheral blood," Abstract, Multiple Sclerosis, Keystone Symposium on Molecular and Cellular Biology, Big Sky, Montana, published online Dec. 11, 2012.
Nakamura, et al., "Clinical features of multiple sclerosis with high plasmablast frequency in peripheral blood," Abstract for Poster Session, Keystone Symposia on Molecular and Cellular Biology, Big Sky, Montana, distributed Jan. 11, 2013.
Shimizu, J., et al., "IFNβ-1b may severely exacerbate Japanese optic-spinal MS in neuromyelitis optica spectrum," *Neurology* 75:1423-1427, AAN Enterprises, Inc., United States (2010).
Srivastava, R., et al., "Potassium Channel KIR4.1 as an Immune Target in Multiple Sclerosis," *The New England Journal of Medicine* 367:115-123, Massachusetts Medical Society, United States (2012).
Tintore, M., et al., "Isolated Demyelinating Syndromes: Comparison of Different MR Imaging Criteria to Predict Conversion to Clinically Definite Multiple Sclerosis," *American Journal of Neuroradiology* 21:702-706, American Society of Neuroradiology, United States (2000).
Waubant, E., et al., "Clinical characteristics of responders to interferon therapy for relapsing MS," *Neurology* 61:184-189, AAN Enterprises, Inc., United States (2003).
Takizawa, H., et al., "Growth Inhibition of Human Lung Cancer Cell Lines by Interleukin 6 in Vitro: A Possible Role in Tumor Growth via an Autocrine Mechanism," *Cancer Research* 53:4175-4181, The American Journal of Cancer Research, United States (1993).
Besse, B., et al., "Phase 2 study of frontline bortezomib in patients with advanced non-small cell lung cancer," *Lung Cancer* 76:78-83, Elsevier Ireland Ltd., Ireland (2011).
Li, T., et al., "Phase II study of the proteasome inhibitor bortezomib (PS-341, Velcade®) in chemotherapy-naïve patients with advanced stage non-small cell lung cancer (NSCLC)," *Lung Cancer* 68:89-93, Elsevier Ireland Ltd., Ireland (2009).
Nakamura, M., et al., "Plasmablast in the Pathology of Multiple Sclerosis," *Jpn. J. Clin. Immounol.* 38(5):403-411, The Japan Society for Clinical Immunology, Japan (2015).
Abiatari, I., et al., "Consensus transcriptome signature of perineural invasion in pancreatic carcinoma," *Mol. Cancer Ther.* 8(6):1494-1504, American Association for Cancer Research, United States (2009).
Demir, I.E., et al., "Nerve-cancer interactions in the stromal biology of pancreatic cancer," *Frontiers in Physiology* 3(Article 97):1-11, Frontiers Media S.A., United States (2012).
Klein, B., et al., "Interleukin-6 in Human Multiple Myeloma," *Blood* 85(4):863-872, American Society of Hematology, United States (1995).

(56) References Cited

OTHER PUBLICATIONS

Koide, N., et al., "Establishment of Perineural Invasion Models and Analysis of Gene Expression Revealed an Invariant Chain (CD74) as a Possible Molecule Involved in Perineural Invasion in Pancreatic Cancer," *Clin. Cancer Res.* 12(8):2419-2426, American Association for Cancer Research, United States (2006).

Märten, A., et al., "Bortezomib is ineffective in an orthotopic mouse model of pancreatic adenocarcinoma," *Mol. Cancer Ther.* 7(11):3624-3631, American Association for Cancer Research, United States (2008).

National Cancer Institute, "SEER Cancer Stat Facts: Pancreas Cancer," https://seer.cancer.gov/statfacts/html/pancreas.html, National Cancer Institute, Bethesda, Maryland, United States, accessed Apr. 25, 2017.

Ozaki, H., et al., "The Prognostic Significance of Lymph Node Metastasis and Intrapancreatic Perineural Invasion in Pancreatic Cancer After Curative Resection," *Jpn. J. Surg.* 29:16-22, Springer-Verlag, United States (1999).

Wang, H., et al., "Phase II Study of Panobinostat and Bortezomib in Patients with Pancreatic Cancer Progressing on Gemcitabine-based Therapy," *Anticancer Research* 32:1027-1032, The International Institute of Anticancer Research, United States (2012).

Bromberg, J., "The IL-6/Jak/Stat3 Pathway: Targeting Metastatic Breast Cancer Research Update," www.mountainsothopefoundation. org (2009).

De Vita, F., et al., "Serum levels of interleukin-6 as a prognostic factor in advanced non-small cell lung cancer," *Oncology Reports* 5:649-652, Spandidos Publications, Greece (1998).

U.S. Appl. No. 15/575,027, 371(c) filed Nov. 17, 2017, Yamamura, T., related application.

U.S. Appl. No. 15/877,894, 371(c) filed Jan. 23, 2018, Maeda, S., related application.

Almand, B., et al., "Clinical Significance of Defective Dendritic Cell Differentiation in Cancer," Clin Cancer Res, 6:1755-1766 (2000).

Almand, B., et al., "Increased Production of Immature Myeloid Cells in Cancer Patients: A Mechanism of Immunosuppression in Cancer," J Immunol, 166:678-689 (2001).

Balint, B., et al., "Alterations of the peripheral B cell compartment in paediatric-onset multiple sclerosis," J Neurol 258(1):S202, Abstract No. P732 (2011).

Cocco, M., et al., "In Vitro Generation of Long-lived Human Plasma Cells," J Immunol, 189:5773-5785 (2012).

Hong, D. S., et al.," Interleukin-6 and Its Receptor in Cancer," Cancer 110:1911-1928 (2007).

Jego, G., et al., "Interleukin-6 is a growth factor for nonmalignant human plasmablasts," Blood 97:1817-1822 (2001).

Jourdan, M., et al., "An in vitro model of differentiation of memory B cells into plasmablasts and plasma cells including detailed phenotypic and molecular characterization," Blood 114:5173-5181 (2009).

Lechner, M. G., et al., "Characterization of Cytokine-Induced Myeloid-Derived Suppressor Cells from Normal Human Peripheral Blood Mononuclear Cells," J Immunol, 185:2273-2284 (2010).

Masui, T., et al., "Expression of IL-6 Receptor in Pancreatic Cancer: Involvement in VEGF Induction," Anticancer Research 22:4093-4100 (2002).

Matsumoto, M., et al., "Interleukin-10-Producing Plasmablasts Exert Regulatory Function in Autoimmune Inflammation," Immunity 41:1040-1051 (2014).

Polman, C. H., et al., "Diagnostic Criteria for Multiple Sclerosis: 2010 Revisions to the McDonald Criteria," Ann Neurol, 69:292-302 (2011).

Shinkeichiryo, "Standard Neurological Therapeutics: Neuromyelitis Optica (NMO)," Japanese Society of Neurological Therapeutics, 30(6):777-794 (2013), with partial English translation.

Wingerchuk, D. M., et al., "Revised diagnostic criteria for neuromyelitis optica," Neurology, 66:1485-1489 (2006).

Wingerchuk, D. M., et al., "International consensus diagnostic criteria for neuromyelitis optica spectrum disorders," Neurology, 85:177-189 (2015).

\* cited by examiner

SEQUENCE LISTING

<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 1
tgagctcaga tatcgggctg aac                                          23

<210> SEQ ID NO 2
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 2
cgtcgtggat gacacagtga tg                                           22

<210> SEQ ID NO 3
<211> LENGTH: 24
<212> TYPE: DNA
<213> ORGANISM: Artificial
<220> FEATURE:

```
<223> OTHER INFORMATION: An artificially synthesized primer sequence

<400> SEQUENCE: 3
gaagcaagtg ggatcaccta tgaa                                          24

<210> SEQ ID NO 4
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 4
ctgtagcctt gagtatggga tgga                                          24

<210> SEQ ID NO 5
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 5
gcaccgtcaa ggctgagaac                                               20

<210> SEQ ID NO 6
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 6
atggtggtga agacgccagt                                               20

<210> SEQ ID NO 7
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 7
ccacttcaca agtcggaggc tta                                           23

<210> SEQ ID NO 8
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 8
gcaagtgcat catcgttgtt catac                                         25

<210> SEQ ID NO 9
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 9
catcatggtg gtggctgtct g                                             21
```

```
<210> SEQ ID NO 10
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 10
cacttccgct tggctcatca                                               20

<210> SEQ ID NO 11
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 11
aaatggtgaa ggtcggtgtg                                               20

<210> SEQ ID NO 12
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 12
tgaaggggtc gttgatgg                                                 18
```

NEUROINVASION INHIBITOR

CROSS-REFERENCE TO RELATED APPLICATIONS

The present application is a U.S. National Stage of International Application No. PCT/JP2009/060314, filed Jun. 5, 2009, which claims priority to JP 2008-147944, filed Jun. 5, 2008.

TECHNICAL FIELD

The present invention relates to neural invasion-suppressing agents. Specifically, the present invention relates to neural invasion-suppressing agents that comprise an interleukin 6 (IL-6) inhibitor as an active ingredient.

BACKGROUND ART

IL-6 is a cytokine also called B-cell stimulating factor 2 (BSF2) or interferon β2. IL-6 was discovered as a differentiation factor involved in the activation of B-cell lymphocytes (Non-Patent Document 1), and was later revealed to be a multifunctional cytokine that influences the function of various cells (Non-Patent Document 2). It has been reported to induce maturation of T lymphocyte cells (Non-Patent Document 3).

IL-6 transmits its biological activity via two kinds of proteins on the cell. The first is the IL-6 receptor, which is a ligand-binding protein to which IL-6 binds, with a molecular weight of about 80 kDa (Non-Patent Documents 4 and 5). The IL-6 receptor is present in a membrane-bound form that penetrates the cell membrane. It is expressed on the cell membrane, and also as a soluble IL-6 receptor, which mainly consists of the extracellular region of the membrane-bound form.

The other kind of protein is the membrane protein gp130, which has a molecular weight of about 130 kDa and is involved in non-ligand binding signal transduction. The biological activity of IL-6 is transmitted into the cell through formulation of an IL-6/IL-6 receptor complex by IL-6 and 11-6 receptor followed by binding of the complex with gp130 (Non-Patent Document 6).

Even today, many pancreatic cancer cases are diagnosed at the advanced and unresectable stage. Furthermore, even in cases that have undergone resection, which is the only way a cure can be expected, pancreatic cancer often recurs early after surgery. Meanwhile, chemotherapy is indicated for unresectable cases with good performance status (PS) and major organ function. However, although chemotherapy is currently a standard therapy, its therapeutic effect is insufficient. For example, even when gemcitabine hydrochloride regarded as the first drug of choice is used, the efficacy rate of palliative effects is 23.8%, the median survival time is 5.7 months, and the one-year survival rate is 18% (foreign phase III clinical trial data). In Japan, 20,000 people are diagnosed as having pancreatic cancer each year, and 22,260 people died of this disease in 2004 (statistics reported by the Ministry of Health, Labour and Welfare), and pancreatic cancer is the fifth cause of cancer death.

Neural invasion is one of the modes of invasion characteristic of pancreatic cancer. The present inventors have revealed that: neural invasion is found in almost 100% of pancreatic cancer cases; it is an important prognostic factor; and it causes functional abnormalities of hepatocytes, and thus is correlated with cachectic symptoms such as anemia, impaired performance status (PS), and undernutrition. Furthermore, neural invasion is thought to be the cause of cancer pain and the like, and there are some reports describing that symptoms were relieved to some extent by irradiating predominant sites of neural invasion, or by excising the nerve upstream of the sites. However, the mechanisms of neural invasion and onset of symptoms caused by neural invasion are poorly understood, and thus there is currently little information on control of neural invasion and symptoms caused by neural invasion. Neural invasion is commonly found regardless of cancer types, and it has been reported as a prognostic factor of prostatic cancer, stomach cancer, and head and neck cancer.

The prior-art documents related to the present invention are shown below.

Non-Patent Document 1: Hirano, T. et al., Nature (1986) 324, 73-76

Non-Patent Document 2: Akira, S. et al., Adv. in Immunology (1993) 54, 1-78

Non-Patent Document 3: Lotz, M. et al., J. Exp. Med. (1988) 167, 1253-1258

Non-Patent Document 4: Taga, T. et al., J. Exp. Med. (1987) 166, 967-981

Non-Patent Document 5: Yamasaki, K. et al., Science (1988) 241, 825-828

Non-Patent Document 6: Taga, T. et al., Cell (1989) 58, 573-581

DISCLOSURE OF THE INVENTION

Problems to be Solved by the Invention

Thus, an objective of the present invention is to provide novel neural invasion-suppressing agents. Furthermore, the present invention provides novel agents for treating pancreatic cancer.

Means for Solving the Problems

The present inventors conducted dedicated studies to achieve the above objectives, and discovered that neural invasion is suppressed by inhibiting IL-6 in a model for neural invasion of pancreatic cancer. Thus, the present invention was completed. The present inventors also demonstrated that an IL-6 receptor is expressed in human pancreatic cancer cell lines, and that IL-6 enhances the chemotactic and migratory activities and intracellular signaling of pancreatic cancer cells, and thus pancreatic cancer can be treated by inhibiting IL-6.

Furthermore, from results of administering IL-6 inhibitors to neural invasion model mice, the present inventors showed that neural invasion of human pancreatic cancer can be suppressed.

More specifically, the present invention provides [1] to [32] below.

[1] An agent for treating pancreatic cancer, which comprises an interleukin 6 (IL-6) inhibitor as an active ingredient.

[2] An agent for suppressing neural invasion of a cell, which comprises an IL-6 inhibitor as an active ingredient.

[3] The agent of [2], which suppresses neural invasion of a cancer cell.

[4] The agent of [3], which suppresses neural invasion of a pancreatic cancer cell.

[5] The agent of any one of [2] to [4], which suppresses neural invasion in the central direction.

[6] The agent of any one of [1] to [5], wherein the IL-6 inhibitor is a substance that binds to an IL-6 receptor.

[7] The agent of [6], wherein the IL-6 inhibitor is an anti-IL-6 receptor antibody.
[8] The agent of [7], wherein the anti-IL-6 receptor antibody is a chimeric, humanized, or human antibody.
[9] A method for treating pancreatic cancer, which comprises the step of administering an IL-6 inhibitor to a subject.
[10] A method for suppressing neural invasion of a cell, which comprises the step of administering an IL-6 inhibitor to a subject.
[11]. The method of [10], which suppresses neural invasion of a cancer cell.
[12] The method of [11], which suppresses neural invasion of a pancreatic cancer cell.
[13] The method of any one of [10] to [12], which suppresses neural invasion in the central direction.
[14]. The method of any one of [9] to [13], wherein the IL-6 inhibitor is a substance that binds to an IL-6 receptor.
[15] The method of [14], wherein the IL-6 inhibitor is an anti-IL-6 receptor antibody.
[16] The method of [15], wherein the anti-IL-6 receptor antibody is a chimeric, humanized, or human antibody.
[17] Use of an IL-6 inhibitor in the production of an agent for treating pancreatic cancer.
[18] Use of an IL-6 inhibitor in the production of an agent for suppressing neural invasion of a cell.
[19] The use of [18], wherein neural invasion of a cancer cell is suppressed.
[20] The use of [19], wherein neural invasion of a pancreatic cancer cell is suppressed.
[21] The use of any one of [18] to [20], wherein neural invasion in the central direction is suppressed.
[22] The use of [17] to [21], wherein the IL-6 inhibitor is a substance that binds to an IL-6 receptor.
[23] The use of [22], wherein the IL-6 inhibitor is an anti-IL-6 receptor antibody.
[24] The use of [23], wherein the anti-IL-6 receptor antibody is a chimeric, humanized, or human antibody.
[25] An IL-6 inhibitor for use in a method for treating pancreatic cancer.
[26] An IL-6 inhibitor for use in a method for suppressing neural invasion of a cell.
[27] The IL-6 inhibitor of [26], which suppresses neural invasion of a cancer cell.
[28] The IL-6 inhibitor of [27], which suppresses neural invasion of a pancreatic cancer cell.
[29] The IL-6 inhibitor of any one of [26] to [28], which suppresses neural invasion in the central direction.
[30] The IL-6 inhibitor of any one of [25] to [29], wherein the IL-6 inhibitor is a substance that binds to an IL-6 receptor.
[31] The IL-6 inhibitor of [30], wherein the IL-6 inhibitor is an anti-IL-6 receptor antibody.
[32] The IL-6 inhibitor of [31], wherein the anti-IL-6 receptor antibody is a chimeric, humanized, or human antibody.

BRIEF DESCRIPTION OF THE DRAWINGS

FIGS. 2A and 2B show results of determining cell growth activity by monitoring the cell count over time.
FIG. 2C shows the result of determining chemotactic activity by chemotaxis assay.
FIG. 2D shows the result of determining migratory activity by wound healing assay.
FIG. 3A shows the intracellular expression of phosphorylated STAT3 protein.
FIG. 3B shows the intracellular expression of phosphorylated Erk1/2 proteins.
FIG. 3C shows the intracellular expression of phosphorylated Akt protein.
FIG. 4A shows a macroscopic image of neural invasion after four weeks.
FIG. 4B is a graph showing the time course of the invasion distance.
FIG. 4C shows a histological image of neural invasion after four weeks.
FIG. 5A shows an image of the neural invasion model.
FIGS. 5B and 5C show the expression levels of mouse IL-6 in the neural invasion model and other models for nerve damage, which were determined by RT-PCR (B) and fluorescent immunostaining (C).
FIG. 9A is a graph showing the invasion distance after administration of the JAK inhibitor AG490. "DMSO" refers to the control group, while "AG490" refers to the AG490 administration group.
FIG. 9B is a graph showing the invasion distance after administration of an anti-IL-6 receptor antibody. "hIgG" refers to the control group, while "MRA" refers to the anti-IL-6 receptor antibody administration group.

MODE FOR CARRYING OUT THE INVENTION

Figure 1:
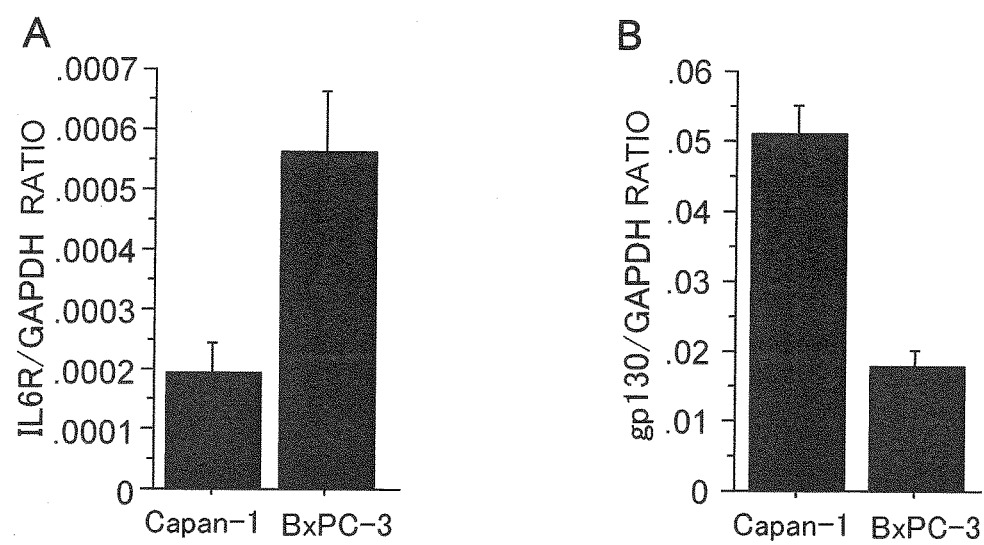
FIG. 1 depicts diagrams showing the expression level of IL-6α receptor (IL6R) mRNA (A), and the expression level of IL-6β receptor (gp130) mRNA (B) in human pancreatic cancer cell lines.

Herein, "IL-6 inhibitor" refers to a substance that blocks IL-6 signaling and inhibits the biological activity of IL-6. Specifically, the IL-6 inhibitors include, for example, substances that bind to IL-6, substances that bind to an IL-6 receptor, and substances that bind to gp130. The IL-6 inhibitors also include substances that inhibit phosphorylation of STAT3 which is important for the intracellular signaling of IL-6, such as AG490. The IL-6 inhibitors include, but are not particularly limited to, anti-IL-6 antibodies, anti-IL-6 receptor antibodies, anti-gp130 antibodies, IL-6 variants, soluble IL-6 receptor variants, partial peptides of IL-6, partial peptides of an IL-6 receptor, and low-molecular-weight compounds having an activity equivalent thereto.
In a preferred embodiment, the IL-6 inhibitors include IL-6 receptor inhibitors, in particular, anti-IL-6 receptor antibodies.

The origin of antibodies used in the present invention is not particularly limited; however, the antibodies are preferably derived from mammals, and more preferably from human.

An antibody of the present invention can be prepared as a polyclonal or monoclonal antibody using known methods. In particular, monoclonal antibodies derived from mammals are preferably used in the present invention. Monoclonal antibodies derived from mammals include those produced by hybridomas and those produced by hosts transformed with an expression vector carrying an antibody gene using genetic engineering techniques. Typically, these antibodies block transmission of the biological activity of IL-6 into cells by binding to IL-6, an IL-6 receptor, gp130, or the like.

Basically, monoclonal antibody-producing hybridomas can be prepared using known techniques as follows. Specifically, immunization is carried out by a conventional immunization method using as a sensitizing antigen an IL-6 receptor, IL-6, gp130, or such. The resulting immune cells are fused with known parental cells by a conventional cell fusion method. Then, monoclonal antibody-producing cells are screened using a conventional screening method.

Specifically, monoclonal antibodies can be produced as follows. For example, when anti-IL-6 receptor antibodies are prepared, a human IL-6 receptor or mouse IL-6 receptor for use as a sensitizing antigen for obtaining antibodies can be obtained by using the IL-6 receptor genes and/or amino acid sequences disclosed in European Patent Application Publication No. EP 325474 and Japanese Patent Application Kokai Publication No. (JP-A) Hei 3-155795, respectively.

There are two kinds of IL-6 receptor proteins: one expressed on the cell membrane and the other separated from the cell membrane (soluble IL-6 receptors) (Yasukawa, K. et al., J. Biochem. (1990) 108, 673-676). The soluble IL-6 receptor essentially consists of the extracellular region of the cell membrane-bound IL-6 receptor, and differs from the membrane-bound IL-6 receptor in that it lacks the transmembrane region or both the transmembrane and intracellular regions. Any IL-6 receptor may be employed as an IL-6 receptor protein, so long as it can be used as a sensitizing antigen for producing an anti-IL-6 receptor antibody used in the present invention.

After transforming an appropriate host cell with a known expression vector system inserted with an IL-6 receptor gene sequence, the desired IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

Likewise, when IL-6 is used as a sensitizing antigen for preparation of antibodies, human IL-6 can be obtained by using the gene and/or amino acid sequences of IL-6 disclosed in Eur. J. Biochem (1987) 168, 543-550, J. Immunol. (1988) 140, 1534-1541, or Agr. Biol. Chem. (1990) 54, 2685-2688. Alternatively, for a sensitizing antigen for preparation of anti-gp130 antibodies, the gene and/or amino acid sequences of gp130 disclosed in European Patent Application Publication No. EP 411946 can be used.

Mammals to be immunized with a sensitizing antigen are not particularly limited, but are preferably selected considering compatibility with the parent cell used for cell fusion. Generally, rodents such as mice, rats, and hamsters are used. Animals are immunized with sensitizing antigens according to known methods. For example, as a general method, animals are immunized by intraperitoneal or subcutaneous injection of a sensitizing antigen. Specifically, the sensitizing antigen is preferably diluted or suspended in an appropriate amount of phosphate-buffered saline (PBS), physiological saline or such, mixed with an appropriate amount of a general adjuvant (e.g., Freund's complete adjuvant), emulsified, and then administered to a mammal several times, every four to 21 days. In addition, an appropriate carrier may be used for immunization with a sensitizing antigen.

Following such immunization, an increased level of a desired antibody in serum is confirmed and then immune cells are obtained from the mammal for cell fusion. Preferred immune cells for cell fusion include, in particular, spleen cells.

The mammalian myeloma cells used as parent cells, i.e. as partner cells to be fused with the above immune cells, include various known cell strains, for example, P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S., J. Exp. Med. (1978) 148, 313-323), 8210 (Galfre, G. et al., Nature (1979) 277, 131-133), and such.

Basically, cell fusion of the aforementioned immune cells and myeloma cells can be performed using known methods, for example, the method of Milstein et al. (Kohler, G and Milstein, C., Methods Enzymol. (1981) 73, 3-46), and such.

More specifically, the aforementioned cell fusion is achieved in general nutrient culture medium in the presence of a cell fusion enhancing agent. For example, polyethylene glycol (PEG), Sendai virus (HVJ), and such are used as fusion enhancing agents. Further, to enhance fusion efficiency, auxiliary agents such as dimethyl sulfoxide may be added depending on the need.

The ratio of immune cells to myeloma cells used is preferably, for example, 1 to 10 immune cells for each myeloma cell. The culture medium used for the aforementioned cell fusion is, for example, the RPMI 1640 or MEM culture medium, which are suitable for proliferation of the aforementioned myeloma cells. A general culture medium used for culturing this type of cell can also be used. Furthermore, serum supplements such as fetal calf serum (FCS) can be used in combination.

For cell fusion, the fusion cells (hybridomas) of interest are formed by mixing predetermined amounts of an aforementioned immune cell and myeloma cell in an aforementioned culture medium, and then adding and mixing a concentration of 30% to 60% (w/v) PEG solution (e.g., a PEG solution with a mean molecular weight of about 1,000 to 6,000) pre-heated to about 37° C. Then, cell fusion agents and such that are unsuitable for the growth of hybridomas can be removed by repeatedly adding an appropriate culture medium and then removing the supernatant by centrifugation.

The above hybridomas are selected by culturing cells in a general selection culture medium, for example, HAT culture medium (a culture medium containing hypoxanthine, aminopterin, and thymidine). Culture in HAT culture medium is continued for a sufficient period, generally several days to several weeks, to kill cells other than the hybridomas of interest (unfused cells). Then, a standard limited dilution method is performed to screen and clone hybridomas that produce an antibody of interest.

In addition to the methods for immunizing non-human animals with antigens for obtaining the aforementioned hybridomas, desired human antibodies with the activity of binding to a desired antigen or antigen-expressing cell can be obtained by sensitizing a human lymphocyte with a desired antigen protein or antigen-expressing cell in vitro, and fusing the sensitized B lymphocyte with a human myeloma cell (e.g., U266) (see, Japanese Patent Application Kokoku Publication No. (JP-B) Hei 1-59878 (examined, approved Japanese patent application published for opposition)). Further, a desired human antibody can be obtained by administering an antigen or antigen-expressing cell to a transgenic animal that has a repertoire of human antibody genes, and then following the aforementioned method (see, International Patent Application Publication Nos. WO 93/12227, WO 92/03918, WO 94/02602, WO 94/25585, WO 96/34096, and WO 96/33735).

The thus-prepared hybridomas which produce monoclonal antibodies can be subcultured in a conventional culture medium and stored in liquid nitrogen for a long period.

When obtaining monoclonal antibodies from the aforementioned hybridomas, the following methods may be employed: (1) methods where the hybridomas are cultured according to conventional methods and the antibodies are obtained as a culture supernatant; (2) methods where the hybridomas are proliferated by administering them to a compatible mammal and the antibodies are obtained as ascites; and so on. The former method is preferred for obtaining antibodies with high purity, and the latter is preferred for large-scale antibody production.

For example, anti-IL-6 receptor antibody-producing hybridomas can be prepared by the method disclosed in JP-A (Kokai) Hei 3-139293. Such hybridomas can be prepared by injecting a PM-1 antibody-producing hybridoma into the abdominal cavity of a BALB/c mouse, obtaining ascites, and then purifying a PM-1 antibody from the ascites; or by culturing the hybridoma in an appropriate medium (e.g., RPMI 1640 medium containing 10% fetal bovine serum, and 5% BM-Condimed H1 (Boehringer Mannheim); hybridoma SFM medium (GIBCO-BRL); PFHM-II medium (GIBCO-BRL), etc.) and then obtaining PM-1 antibody from the culture supernatant.

Recombinant antibodies can be used as the monoclonal antibodies of the present invention, wherein the antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., Therapeutic Monoclonal Antibodies, published in the United Kingdom by Macmillan Publishers Ltd, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using the an mRNA Purification Kit (Pharmacia) and such. Alternatively, mRNAs can be directly prepared using a QuickPrep mRNA Purification Kit (Pharmacia).

cDNAs of the antibody V regions are synthesized from the obtained mRNAs using reverse transcriptase. cDNAs may be synthesized using an AMV Reverse Transcriptase First-strand cDNA Synthesis Kit and so on. Further, to synthesize and amplify the cDNAs, the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and PCR may be employed. A DNA fragment of interest is purified from the obtained PCR products and then ligated with a vector DNA. Then, a recombinant vector is prepared using the above DNA and introduced into *Escherichia coli* or such, and then its colonies are selected to prepare a desired recombinant vector. The nucleotide sequence of the DNA of interest is confirmed by, for example, the dideoxy method.

When a DNA encoding the V region of an antibody of interest is obtained, the DNA is ligated with a DNA that encodes a desired antibody constant region (C region), and inserted into an expression vector. Alternatively, a DNA encoding an antibody V region may be inserted into an expression vector comprising a DNA of an antibody C region.

To produce an antibody to be used in the present invention, as described below, an antibody gene is inserted into an expression vector such that it is expressed under the control of an expression regulating region, for example, an enhancer and promoter. Then, the antibody can be expressed by transforming a host cell with this expression vector.

In the present invention, to reduce heteroantigenicity against humans and such, artificially modified genetic recombinant antibodies, for example, chimeric antibodies, humanized antibodies, or such, can be used. These modified antibodies can be prepared using known methods.

A chimeric antibody can be obtained by ligating a DNA encoding an antibody V region, obtained as above, with a DNA encoding a human antibody C region, then inserting the DNA into an expression vector and introducing it into a host for production (see, European Patent Application Publication No. EP 125023; International Patent Application Publication No. WO 92/19759). This known method can be used to obtain chimeric antibodies useful for the present invention.

Humanized antibodies are also referred to as reshaped human antibodies, and are antibodies wherein the complementarity determining regions (CDRs) of an antibody from a mammal other than human (e.g., a mouse antibody) are transferred into the CDRs of human antibodies. General methods for this gene recombination are also known (see, European Patent Application Publication No. EP 125023, International Patent Application Publication No. WO 92/19759).

More specifically, DNA sequences designed such that the CDRs of a mouse antibody are ligated with the framework regions (FRs) of a human antibody are synthesized by PCR from several oligonucleotides produced to contain overlapping portions at their termini. The obtained DNA is ligated with a human antibody C region-encoding DNA and then inserted into an expression vector. The expression vector is introduced into a host to produce the humanized antibody (see, European Patent Application Publication No. EP 239400, International Patent Application Publication No. WO 92/19759).

The human antibody FRs to be ligated via the CDRs are selected so that the CDRs form suitable antigen binding sites. The amino acid(s) within the FRs of the antibody variable regions may be substituted as necessary so that the CDRs of the reshaped human antibody form an appropriate antigen binding site (Sato, K. et al., Cancer Res. (1993) 53, 851-856).

Human antibody heavy chain C regions are generally used for the chimeric and humanized antibodies, and include $C\gamma$ etc. For example, Cγ1, Cγ2, Cγ3, or Cγ4 may be used. Human antibody light chain C regions include, for example, Gκ and Cλ. Furthermore, to improve the stability of the antibodies or their production, the human antibody C regions may be modified.

Chimeric antibodies consist of the variable region of an antibody derived from a non-human mammal and the constant region of an antibody derived from a human; humanized antibodies consist of the CDRs of an antibody derived from a non-human mammal and the framework regions and constant regions derived from a human antibody. They have reduced antigenicity in the human body, and are thus useful as antibodies for use as pharmaceuticals.

Preferred specific examples of humanized antibodies for use in the present invention include the humanized PM-1 antibody (see, International Patent Application Publication No. WO 92/19759).

Furthermore, in addition to the aforementioned methods for obtaining human antibodies, techniques for obtaining human antibodies by panning using a human antibody library are also known. For example, the variable regions of human antibodies can be expressed on phage surfaces as single chain antibodies (scFv) by using the phage display method, and antigen-binding phages can then be selected. By analyzing the genes of the selected phages, DNA sequences coding for the human antibody variable regions that bind to the antigen can be determined Once the DNA sequence of an scFv that binds to the antigen is revealed, an appropriate expression vector comprising the sequence can be constructed to obtain a human antibody. These methods are already known, and the publications of WO 92/01047, WO 92/20791, WO93/06213, WO 93/11236, WO 93/19172, WO 95/01438, and WO 95/15388 can be used as reference.

The antibody genes constructed above can be expressed according to conventional methods. When a mammalian cell is used, the antibody gene can be expressed using a DNA in which the antibody gene to be expressed is functionally ligated to a useful commonly used promoter and a poly A signal downstream of the antibody gene, or a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and also include mammalian cell-derived promoters/enhancers such as human elongation factor 1α (HEF1α).

For example, when the SV40 promoter/enhancer is used, the expression can be easily performed by following the method by Mulligan et al. (Mulligan, R. C. et al., Nature (1979) 277, 108-114). Alternatively, in the case of the HEF1α promoter/enhancer, the method by Mizushima et al. (Mizushima, S. and Nagata S., Nucleic Acids Res. (1990) 18, 5322) can be easily used.

Production systems using prokaryotic cells include those using bacterial cells. Known bacterial cells include *E. coli* and *Bacillus subtilis*.

When *E. coli* is used, an antibody gene can be expressed by functionally ligating a conventional promoter, a signal sequence for antibody secretion, and the antibody gene to be expressed. Examples of the promoter include a lacZ promoter, araB promoter and such. When a lacZ promoter is used, genes can be expressed according to the method of Ward et al. (Ward, E. S. et al., Nature (1989) 341, 544-546; Ward, E. S. et al., FASEB J. (1992) 6, 2422-2427); and the araB promoter may be used according to the method of Better et al. (Better, M. et al., Science (1988) 240, 1041-1043).

When the antibody is produced into the periplasm of *E. coli*, the pel B signal sequence (Lei, S. P. et al., J. Bacteriol. (1987) 169, 4379-4383) may be used as a signal sequence for antibody secretion. The antibodies produced into the periplasm are isolated, and then used after appropriately refolding the antibody structure (see, for example, WO 96/30394).

As the replication origin, those derived from SV40, polyoma virus, adenovirus, bovine papilloma virus (BPV) and such may be used. In addition, to enhance the gene copy number in a host cell system, the expression vector may comprise the aminoglycoside phosphotransferase (APH) gene, thymidine kinase (TK) gene, *E. coli* xanthine-guanine phosphoribosyltransferase (Ecogpt) gene, dihydrofolate reductase (dhfr) gene, or such as a selection marker.

Any production system may be used to prepare the antibodies for use in the present invention. The production systems for antibody preparation include in vitro and in vivo production systems. In vitro production systems include those using eukaryotic cells or prokaryotic cells.

When eukaryotic cells are used as hosts, the production systems include those using animal cells, plant cells, or fungal cells. Such animal cells include (1) Mammalian cells, for example, CHO, COS, myeloma, baby hamster kidney (BHK), HeLa, Vero, and such; (2) amphibian cells, for example, *Xenopus oocyte*; and (3) insect cells, for example, sf9, sf21, Tn5, and such. Known plant cells include cells derived from *Nicotiana tabacum*, which may be cultured as a callus. Known fungal cells include yeasts such as *Saccharomyces* (e.g., *S. cerevisiae*), mold fungi such as *Aspergillus* (e.g., *A. niger*), and such.

Antibodies can be obtained by using transformation to introduce an antibody gene of interest into these cells, and then culturing the transformed cells in vitro. Cultures are conducted according to known methods. For example, DMEM, MEM, RPMI 1640, IMDM may be used as the culture medium, and serum supplements such as FCS may be used in combination. Further, cells introduced with antibody genes may be transferred into the abdominal cavity or such of an animal to produce the antibodies in vivo.

On the other hand, in vivo production systems include those using animals or plants. Production systems using animals include those that use mammals or insects. Mammals that can be used include goats, pigs, sheep, mice, bovines and such (Vicki Glaser, SPECTRUM Biotechnology Applications, 1993). Further, insects that can be used include silkworms. When using plants, tobacco may be used, for example.

An antibody gene is introduced into these animals or plants, the antibody is produced in the body of the animals or plants, and this antibody is then recovered. For example, an antibody gene can be prepared as a fusion gene by inserting it into the middle of a gene encoding a protein such as goat β casein, which is uniquely produced into milk. DNA fragments comprising the fusion gene, which includes the antibody gene, are injected into goat embryos, and the embryos are introduced into female goats. The desired antibody is obtained from milk produced by the transgenic animals born to the goats that received the embryos, or produced from progenies of these animals. The transgenic goats can be given hormones to increase the volume of milk containing the desired antibody that they produce (Ebert, K. M. et al., Bio/Technology (1994) 12, 699-702).

When silkworms are used, the silkworms are infected with a baculovirus inserted with a desired antibody gene, and the desired antibody is obtained from the body fluids of these silkworm (Maeda, S. et al., Nature (1985) 315, 592-594). Moreover, when tobacco is used, the desired antibody gene is inserted into a plant expression vector (e.g., pMON530) and the vector is introduced into bacteria such as *Agrobacterium tumefaciens*. This bacterium is used to infect tobacco (e.g., *Nicotiana tabacum*) such that desired antibodies can be obtained from the leaves of this tobacco (Julian, K.-C. Ma et al., Eur. J. Immunol. (1994) 24, 131-138).

When producing antibodies using in vitro or in vivo production systems, as described above, DNAs encoding an antibody heavy chain (H chain) and light chain (L chain) may be inserted into separate expression vectors and a host is then co-transformed with the vectors. Alternatively, the DNAs may be inserted into a single expression vector for transforming a host (see International Patent Application Publication No. WO 94/11523).

The antibodies used in the present invention may be antibody fragments or modified products thereof, so long as they can be suitably used in the present invention. For example, antibody fragments include Fab, F(ab')2, Fv, and single chain Fv (scFv), in which the Fvs of the H and L chains are linked via an appropriate linker.

Specifically, the antibody fragments are produced by treating antibodies with enzymes, for example, papain or pepsin, or alternatively, genes encoding these fragments are constructed, introduced into expression vectors, and these are expressed in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; Bird, R. E. et al., TIBTECH (1991) 9, 132-137).

An scFv can be obtained by linking the H-chain V region and the L-chain V region of an antibody. In the scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, arbitrary single chain peptides consisting of 12 to 19 amino acid residues.

An scFv-encoding DNA can be obtained by using a DNA encoding an H chain or a V region and a DNA encoding an L chain or a V region of the aforementioned antibodies as templates, using PCR to amplify a DNA portion that encodes the desired amino acid sequence in the template sequence and uses primers that define the termini of the portion, and then further amplifying the amplified DNA portion with a DNA that encodes a peptide linker portion and primer pairs that link both ends of the linker to the H chain and L chain.

Once an scFv-encoding DNA has been obtained, an expression vector comprising the DNA and a host transformed with the vector can be obtained according to conventional methods. In addition, scFv can be obtained according to conventional methods using the host.

As above, these antibody fragments can be produced from the host by obtaining and expressing their genes. Herein, an "antibody" encompasses such antibody fragments.

Antibodies bound to various molecules, such as polyethylene glycol (PEG), may also be used as modified antibodies. Herein, an "antibody" encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and/or purified using affinity chromatography. Columns to be used for the affinity chromatography include, for example, protein A columns and protein G columns. Carriers used for the protein A columns include, for example, HyperD, POROS, Sepharose FF and such. In addition to the above, other methods used for the isolation and/or purification of common proteins may be used, and are not limited in any way.

For example, the antibodies used for the present invention may be isolated and/or purified by appropriately selecting and combining chromatographies in addition to affinity chromatography, filters, ultrafiltration, salting-out, dialysis, and such. Chromatographies include, for example, ion-exchange chromatography, hydrophobic chromatography, gel filtration, and such. These chromatographies can be applied to high performance liquid chromatography (HPLC). Alternatively, reverse phase HPLC may be used.

The concentration of the antibodies obtained as above can be determined by absorbance measurement, ELISA, or such. Specifically, absorbance is determined by appropriately diluting the antibody solution with PBS(−), measuring absorbance at 280 nm, and calculating the concentration (1.35 OD=1 mg/ml). Alternatively, when using ELISA, the measurement can be performed as follows: Specifically, 100 µl of goat anti-human IgG (TAG) diluted to 1 µg/ml with 0.1 M bicarbonate buffer (pH 9.6) is added to a 96-well plate (Nunc) and incubated overnight at 4° C. to immobilize the antibody. After blocking, 100 µl of an appropriately diluted antibody of the present invention or an appropriately diluted sample comprising the antibody, and human IgG (CAPPEL) are added as a standard, and incubated for one hour at room temperature.

After washing, 100 µl of 5,000× diluted alkaline phosphatase-labeled anti-human IgG (BIO SOURCE) is added and incubated for one hour at room temperature. After another wash, substrate solution is added and incubated, and the absorbance at 405 nm is measured using a Microplate Reader Model 3550 (Bio-Rad) to calculate the concentration of the antibody of interest.

Specifically, examples of anti-IL-6 antibodies include, but are not particularly limited to, the antibodies MH166 (Matsuda, T. et al., Eur. J. Immunol. (1998) 18, 951-956) and SK2 (Sato K et al., The abstracts of the 21st Annual Meeting of the Japanese Society for Immunology (1991) 21, 166).

Specifically, examples of anti-IL-6 receptor antibodies include, but are not particularly limited to, the antibodies MR16-1 (Tamura, T. et al., Proc. Natl. Acad. Sci. USA (1993) 90, 11924-11928), PM-1 (Hirata, Y. et al., J. Immunol. (1989) 143, 2900-2906), AUK12-20, AUK64-7, and AUK146-15 (International Patent Application No. WO 92-19759). Of these, the PM-1 antibody is an example of preferred monoclonal antibodies against the human IL-6 receptor, while the MR16-1 antibody is an example of preferred monoclonal antibodies against the mouse IL-6 receptor; however, the antibodies are not limited thereto. Examples of preferred humanized anti-IL-6 receptor antibodies include a humanized PM-1 antibody (Tocilizumab; MRA). Other preferred humanized anti-IL-6 receptor antibodies include, for example, the antibodies described in WO2009/041621. In another preferred embodiment, anti- IL-6 receptor antibodies include those that recognize the same epitope recognized by a humanized PM-1 antibody (Tocilizumab; MRA).

Specifically, examples of anti-gp130 antibodies include, but are not particularly limited to, the antibodies AM64 (JP-A (Kokai) Hei 3-219894), 4B11, 2H4 (U.S. Pat. No. 5,571,513), and B-P8 (JP-A (Kokai) Hei 8-291199).

The IL-6 variants used in the present invention are substances with the activity of binding to an IL-6 receptor and which do not transmit IL-6 biological activity. That is, the IL-6 variants compete with IL-6 to bind to IL-6 receptors, but fail to transmit IL-6 biological activity, and thus block IL-6-mediated signal transduction.

The IL-6 variants are produced by introducing mutation(s) by substituting amino acid residues in the amino acid sequence of IL-6. The origin of IL-6 used as the base of the IL-6 variants is not limited, but is preferably human IL-6, considering antigenicity and such.

More specifically, amino acid substitutions are performed by predicting the secondary structure of the IL-6 amino acid sequence using known molecular modeling programs (e.g., WHATIF; Vriend et al., J. Mol. Graphics (1990) 8, 52-56), and further assessing the influence of the substituted amino acid residue(s) on the whole molecule. After determining the appropriate amino acid residue to be substituted, commonly performed PCR methods are carried out using a nucleotide sequence encoding a human IL-6 gene as a template, and mutations are introduced to cause amino acids substitutions, and thus genes encoding IL-6 variants are obtained. If needed, this gene is inserted into an appropriate expression vector, and the IL-6 variant can be obtained by applying the aforementioned methods for expression, production, and purification of recombinant antibodies.

Specific examples of the IL-6 variants are those disclosed in Brakenhoff et al., J. Biol. Chem. (1994) 269, 86-93, Savino et al., EMBO J. (1994) 13, 1357-1367, WO 96/18648, and WO 96/17869.

The IL-6 receptor partial peptides are peptides that comprise part or all of the amino acid sequence of the region of the IL-6 receptor amino acid sequence that is involved in the binding between the IL-6 and IL-6 receptor. Such peptides usually comprise ten to 80, preferably 20 to 50, more preferably 20 to 40 amino acid residues.

The IL-6 receptor partial peptides can be produced according to generally known methods, for example, genetic engineering techniques or peptide synthesis methods, by specifying the region of the IL-6 receptor amino acid sequence that is involved in the binding between the IL-6 and IL-6 receptor, and using a portion or entirety of the amino acid sequence of the specified region.

When preparing an IL-6 receptor partial peptide using genetic engineering methods, a DNA sequence encoding the desired peptide is inserted into an expression vector, and then the peptide can be obtained by applying the aforementioned methods for expressing, producing, and purifying recombinant antibodies.

When producing an IL-6 receptor partial peptide by using peptide synthesis methods, generally used peptide synthesis methods, for example, solid phase synthesis methods or liquid phase synthesis methods, may be used.

Specifically, the peptides can be synthesized according to the method described in "Continuation of Development of Pharmaceuticals, Vol. 14, Peptide Synthesis (in Japanese) (ed. Haruaki Yajima, 1991, Hirokawa Shoten)". As a solid phase synthesis method, for example, the following method can be employed: the amino acid corresponding to the C terminus of the peptide to be synthesized is bound to a support that is insoluble in organic solvents, then the peptide strand is elongated by alternately repeating (1) the reaction of condensing amino acids, whose α-amino groups and branch chain functional groups are protected with appropriate protecting groups, one at a time in a C- to N-terminal direction; and (2) the reaction of removing the protecting groups from the α-amino groups of the resin-bound amino acids or peptides. Solid phase peptide synthesis is broadly classified into the Boc method and the Fmoc method, depending on the type of protecting groups used.

After synthesizing a protein of interest as above, deprotection reactions are carried out, then the peptide strand is cleaved from its support. For the cleavage reaction of the peptide strand, hydrogen fluoride or trifluoromethane sulfonic acid are generally used for the Boc method, and TFA is generally used for the Fmoc method. In the Boc method, for example, the above-mentioned protected peptide resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, on the other hand, the deprotection reaction and the reaction to cleave the peptide strand from the support can be performed in TFA using a method similar to those described above, for example.

Obtained crude peptides can be separated and/or purified by applying HPLC. Elution may be performed under optimum conditions using a water-acetonitrile solvent system, which is generally used for protein purification. The fractions corresponding to the peaks of the obtained chromatographic profile are collected and freeze-dried. Thus, purified peptide fractions are identified by molecular weight analysis via mass spectrum analysis, amino acid composition analysis, amino acid sequence analysis, or such.

The IL-6 inhibitors of the present invention can be used to suppress neural invasion. Herein, "neural invasion" refers to a mode of cell invasion and growth in nerve tissues by cancer cells or other types of cells, and this sometimes accompanies tissue destruction (destructive growth) or such. In the present invention, preferred neural invasion includes neural invasion by cancer cells. When cancer cell invasion is suppressed, there is no particular limitation on the type of target cancer. The cancer may be of any type including pancreatic cancer, stomach cancer, prostatic cancer, head and neck cancer, breast cancer, lung cancer, colon cancer, and ovarian cancer. However, it is preferable to suppress invasion of pancreatic cancer cells. It is possible to suppress neural invasion in either the central or peripheral direction. However, it is preferable to suppress neural invasion in the central direction (for example, neural invasion from a nerve damage site to the central side) because pancreatic cancer cells tend to invade nerves in the central direction.

Herein, "suppression of neural invasion" refers to suppression of the occurrence of neural invasion, reduction of the incidence of neural invasion, reduction of the distance of neural invasion, retardation of the rate of neural invasion, or the like.

Various symptoms associated with neural invasion (for example, pain such as cancer pain, anemia, impairment of performance status (PS), and undernutrition) can be treated or suppressed by suppressing neural invasion using an IL-6 inhibitor of the present invention. Thus, the present invention also includes agents for treating or suppressing various symptoms associated with neural invasion, which comprise an IL-6 inhibitor.

The therapeutic agents for pancreatic cancer of the present invention can be used in the treatment and/or prevention of pancreatic cancer.

Herein, "treatment of pancreatic cancer" refers to suppression of the development of pancreatic cancer, reduction of the incidence of pancreatic cancer, suppression of the growth of pancreatic cancer cells, shrinkage of pancreatic cancer tissues, amelioration of pancreatic cancer symptoms, suppression of pancreatic cancer metastasis, or the like.

The effects of IL-6 inhibitors used in the present invention can be assessed, for example, using the activity of inhibiting the signaling as an indicator. However, the assessment methods are not limited thereto. The activity of IL-6 inhibitors in inhibiting the signal transduction can be evaluated by conventional methods. Specifically, IL-6 is added to cultures of IL-6-dependent human myeloma cell lines (S6B45 and KPMM2), human Lennert T lymphoma cell line KT3, or IL-6-dependent cell line MH60.BSF2; and the $^3$H-thymidine uptake by the IL-6-dependent cells is measured in the presence of an IL-6 inhibitor. Alternatively, IL-6 receptor-expressing U266 cells are cultured, and $^{125}$I-labeled IL-6 and an IL-6 inhibitor are added to the culture at the same time; and then $^{125}$I-labeled IL-6 bound to the IL-6 receptor-expressing cells is quantified. In addition to the IL-6 inhibitor group, a negative control group that does not contain an IL-6 inhibitor is included in the assay system described above. The activity of the IL-6 inhibitor to inhibit IL-6 can be evaluated by comparing the results of both groups.

Subjects to be administered with the therapeutic or suppressing agents of the present invention are mammals. The mammals are preferably humans.

The therapeutic or suppressing agents of the present invention can be administered as pharmaceuticals, and may be administered systemically or locally via oral or parenteral administration. For example, intravenous injections such as drip infusions, intramuscular injections, intraperitoneal injections, subcutaneous injections, suppositories, enemas, oral enteric tablets, or the like can be selected. Appropriate administration methods can be selected depending on a patient's age and symptoms. The effective dose per administration is selected from the range of 0.01 to 100 mg/kg body weight. Alternatively, the dose may be selected from the range of 1 to 1000 mg/patient, preferably from the range of 5 to 50 mg/patient. A preferred dose and administration method are as follows: For example, when an anti-IL-6 receptor antibody is used, the effective dose is an amount such that free antibody is present in the blood. Specifically, a dose of 0.5 to 40 mg/kg body weight/month (four weeks), preferably 1 to 20 mg/kg body weight/month is administered via an intravenous injection such as a drip infusion, subcutaneous injection or such, once to several times a month, for example, twice a week, once a week, once every two weeks, or once every four weeks. The administration schedule may be adjusted by, for example, extending the administration interval of twice a week or once a week to once every two weeks, once every three weeks, or once every four weeks, while monitoring the condition of the patient and changes in the blood test values.

The therapeutic agents and suppressing agents of the present invention may contain pharmaceutically acceptable carriers such as preservatives and stabilizers. "Pharmaceutically acceptable carrier" refers to a material that can be administered in combination with the above agents.

Such pharmaceutically acceptable materials include, for example, sterile water, physiological saline, stabilizers, excipients, buffers, preservatives, detergents, chelating agents (EDTA and such), and binders.

In the present invention, detergents include non-ionic detergents, and typical examples of such include sorbitan fatty acid esters such as sorbitan monocaprylate, sorbitan monolaurate, and sorbitan monopalmitate; glycerin fatty acid esters such as glycerin monocaprylate, glycerin monomyristate and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives such as polyoxyethylene sorbit beeswax; polyoxyethylene lanolin derivatives such as polyoxyethylene lanolin; and polyoxyethylene fatty acid amides and such with an HLB of six to 18, such as polyoxyethylene stearic acid amide.

Detergents also include anionic detergents, and typical examples of such include, for example, alkylsulfates having an alkyl group with ten to 18 carbon atoms, such as sodium cetylsulfate, sodium laurylsulfate, and sodium oleylsulfate; polyoxyethylene alkyl ether sulfates in which the alkyl group has ten to 18 carbon atoms and the average molar number of added ethylene oxide is 2 to 4, such as sodium polyoxyethylene lauryl sulfate; alkyl sulfosuccinate ester salts having an alkyl group with eight to 18 carbon atoms, such as sodium lauryl sulfosuccinate ester; natural detergents, for example, lecithin; glycerophospholipids; sphingophospholipids such as sphingomyelin; and sucrose fatty acid esters in which the fatty acids have 12 to 18 carbon atoms.

One, two or more of the detergents described above can be combined and added to the agents of the present invention. Detergents that are preferably used in the preparations of the present invention include polyoxyethylene sorbitan fatty acid esters, such as polysorbates 20, 40, 60, and 80. Polysorbates 20 and 80 are particularly preferred. Polyoxyethylene polyoxypropylene glycols, such as poloxamer (Pluronic F-68® and such), are also preferred.

The amount of detergent added varies depending on the type of detergent used. When polysorbate 20 or 80 is used, the amount is in general in the range of 0.001 to 100 mg/ml, preferably in the range of 0.003 to 50 mg/ml, more preferably in the range of 0.005 to 2 mg/ml.

In the present invention, buffers include phosphate, citrate buffer, acetic acid, malic acid, tartaric acid, succinic acid, lactic acid, potassium phosphate, gluconic acid, capric acid, deoxycholic acid, salicylic acid, triethanolamine, fumaric acid, and other organic acids; and carbonic acid buffer, Tris buffer, histidine buffer, and imidazole buffer.

Liquid preparations may be formulated by dissolving the agents in aqueous buffers known in the field of liquid preparations. The buffer concentration is in general in the range of 1 to 500 mM, preferably in the range of 5 to 100 mM, more preferably in the range of 10 to 20 mM.

The agents of the present invention may also comprise other low-molecular-weight polypeptides; proteins such as serum albumin, gelatin, and immunoglobulin; amino acids; sugars and carbohydrates such as polysaccharides and monosaccharides, sugar alcohols, and such.

Herein, amino acids include basic amino acids, for example, arginine, lysine, histidine, and ornithine, and inorganic salts of these amino acids (preferably hydrochloride salts, and phosphate salts, namely phosphate amino acids). When free amino acids are used, the pH is adjusted to a preferred value by adding appropriate physiologically acceptable buffering substances, for example, inorganic acids, and in particular hydrochloric acid, phosphoric acid, sulfuric acid, acetic acid, and formic acid, and salts thereof. In this case, the use of phosphate is particularly beneficial because it gives quite stable freeze-dried products. Phosphate is particularly advantageous when preparations do not substantially contain organic acids, such as malic acid, tartaric acid, citric acid, succinic acid, and fumaric acid, or do not contain corresponding anions (malate ion, tartrate ion, citrate ion, succinate ion, fumarate ion, and such). Preferred amino acids are arginine, lysine, histidine, and ornithine. Acidic amino acids can also be used, for example, glutamic acid and aspartic acid, and salts thereof (preferably sodium salts); neutral amino acids, for example, isoleucine, leucine, glycine, serine, threonine, valine, methionine, cysteine, and alanine; and aromatic amino acids, for example, phenylalanine, tyrosine, tryptophan, and its derivative, N-acetyl tryptophan.

Herein, sugars and carbohydrates such as polysaccharides and monosaccharides include, for example, dextran, glucose, fructose, lactose, xylose, mannose, maltose, sucrose, trehalose, and raffinose.

Herein, sugar alcohols include, for example, mannitol, sorbitol, and inositol.

When the agents of the present invention are prepared as aqueous solutions for injection, the agents may be mixed with, for example, physiological saline, and/or isotonic solution containing glucose or other auxiliary agents (such as D-sorbitol, D-mannose, D-mannitol, and sodium chloride). The aqueous solutions may be used in combination with appropriate solubilizing agents such as alcohols (ethanol and such), polyalcohols (propylene glycol, PEG, and such), or non-ionic detergents (polysorbate 80 and HCO-50).

The agents may further comprise, if required, diluents, solubilizers, pH adjusters, soothing agents, sulfur-containing reducing agents, antioxidants, and such.

Herein, the sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having one to seven carbon atoms.

Moreover, the antioxidants in the present invention include, for example, erythorbic acid, dibutylhydroxy toluene, butylhydroxy anisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

If required, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science $16^{th}$ edition", Oslo Ed., 1980, and the like). Furthermore, methods for preparing agents as sustained-release agents are also known, and are applicable to the present invention (Langer et al., J. Biomed. Mater. Res. 1981, 15: 167-277; Langer, Chem. Tech. 1982, 12: 98-105; U.S. Pat. No. 3,773,919; European Patent Application No. (EP) 58,481; Sidman et al., Biopolymers 1983, 22: 547-556; and EP 133,988).

Pharmaceutically acceptable carriers used are appropriately selected from those described above or combined depending on the type of dosage form, but are not limited thereto.

The present invention relates to methods for suppressing neural invasion in a subject who has developed or can develop neural invasion, which comprise the step of administering an IL-6 inhibitor to the subject.

The present invention also relates to methods for treating and/or preventing pancreatic cancer in a subject who has developed or can develop pancreatic cancer, which comprise the step of administering an IL-6 inhibitor to the subject.

Herein, the "subject" refers to the organisms or organism body parts to be administered with a therapeutic or suppressing agent of the present invention. The organisms include animals (for example, human, domestic animal species, and wild animals) but are not particularly limited.

The "organism body parts" preferably include disease sites, but are not particularly limited thereto.

Herein, "administration" includes oral and parenteral administration. Oral administration includes, for example, administration of oral agents. Such oral agents include, for example, granules, powders, tablets, capsules, solutions, emulsions, and suspensions.

Parenteral administration includes, for example, administration of injections. Such injections include, for example, subcutaneous injections, intramuscular injections, and intraperitoneal injection. Meanwhile, the effects of the methods of the present invention can be achieved by introducing genes comprising oligonucleotides to be administered to living bodies using gene therapy techniques. Alternatively, the agents of the present invention may be administered locally to intended areas of treatment. For example, the agents can be administered by local injection during surgery, use of catheters, or targeted gene delivery of DNAs encoding peptides of the present invention.

When a method of the present invention is carried out, an agent of the present invention may be administered as a portion of a pharmaceutical composition, together with at least one other agent (for example, other neural invasion-suppressing agents and other therapeutic agents for pancreatic cancer). In an embodiment, the agents of the present invention and other agents may be administered substantially simultaneously.

All prior art documents cited in this specification are incorporated herein by reference.

EXAMPLES

Hereinbelow, the present invention will be specifically described with reference to the Examples, but it is not to be construed as being limited thereto. Various alterations and modifications can be made by those skilled in the art. Such alterations and modifications are also included in the present invention.

Materials and Methods

Cells

Capan-1 and BxPC-3, which are human pancreatic cancer cell lines, were purchased from the American Type Culture Collection (ATCC). According to the manual recommended by ATCC, the cells were cultured and passaged using an incubator capable of maintaining a temperature of 37° C. under 5% $CO_2$.

Determination of Cell Count

Cells were harvested from dishes, and viable cells were counted using trypan blue and a hemocytometer.

Chemotaxis Assay

Cell culture inserts (BD Falcon) having 8-μm pores in the bottom surface were inserted into 24 wells. The cell culture inserts and wells were used as upper and lower chambers, respectively. Human recombinant IL-6 (hrIL6) vehicles were prepared at 0, 1, 10, and 100 ng/ml using hrIL6 (R&D systems) and serum-free culture medium. 600 μl of the hrIL6 vehicles was added to the lower chambers. 100 μl of a cell suspension ($2 \times 10^6$ cells/ml) was added to the upper chambers. After 24 hours of incubation, cells that passed through the pores were counted. This assay was carried out twelve times for each group. The cell count was divided by the average number of cells that passed through the pores at 0 ng/ml hrIL6. The resulting normalized values were recorded.

Wound Healing Assay 1 ml of a cell suspension ($3 \times 10^5$ cells/ml) was added to each of 24 wells, and incubated for 24 hours. Then, the medium was replaced with serum-free medium. After 24 hours of incubation, a strip-shaped cell-free area was produced by scraping the central area of the well with a glass rod. After measuring the width of the strip, the medium was replaced with an hrIL6 vehicle at 0, 1, 10, or 100 ng/ml. After 24 hours of incubation, changes in the width of the cell-free area were determined. This assay was carried out twelve times for each group. The determined values were divided by the average width change at 0 ng/ml hrIL6. The resulting normalized values were recorded.

Antibody

Western blotting was carried out using the following primary antibodies: anti-phosphorylated STAT3 antibody (Santa Cruz), anti-STAT3 antibody (Santa Cruz), anti-phosphorylated Erk1/2 antibody (Cell Signaling), anti-Erk1/2 antibody (Cell Signaling), anti-phosphorylated Akt antibody (Cell Signaling), anti-Akt antibody (Cell Signaling), and anti-actin antibody (Santa Cruz). Fluorescent immunostaining was carried out using the following primary antibodies: anti-S100 antibody (DAKO) and anti-mouse IL-6 antibody (Santa Cruz). Nuclear staining was performed using DRAQ5 (AXXORA). Immunostaining was performed using an anti-phosphorylated STAT3 antibody (Santa Cruz).

Western Blotting

Cell lysates were prepared using a lysate buffer (20 mM Hepes-NaOH (pH 7.0), 0.5% NP-40, 15% Glycerol, 300 mM NaCl, 1 mM EDTA, 10 mM NaF). The protein concentration was determined using a BCA Protein Assay Kit (PIERCE). Then, cell lysates containing 20 mg of protein were electrophoresed in 7.5% or 12% acrylamide gels. The proteins were transferred onto a polyvinylidene difluoride membrane (Millipore). An antibody was added to the membrane, and the protein expression was visualized using Enhanced Chemiluminescence Reagent (Amersham Biosciences).

Immunostaining of Phosphorylated STAT3 and Its Assessment Method

Antigen activation was performed by heat treatment at 95° C. for ten minutes in 10 mM citrate buffer using a microwave. DAB was used for the chromogenic reaction. Four weeks after preparation of neural invasion model mice, 26 sciatic nerves were isolated from 26 mice, and used as samples. In the areas of interest, i.e., the central and peripheral ends of an area of neural invasion, the numbers of cancer cells and phosphorylated STAT3-positive cancer cells were counted in each visual field using a 40× objective lens. The labeling index was determined according to the following formula:

[Number of phosphorylated STAT3-positive cancer cells]/[Number of cancer cells].

Neural Invasion Model

Six-week-old male mice with severe combined immune deficiency (SCID) were used. The mice were anesthetized by administering barbital at 50 mg/kg into their peritoneal cavities. After exposing the left sciatic nerves, 2.5 μl of a suspension of cancer cells ($1.0 \times 10^4$ cells/μl) was injected directly into the sciatic nerves using a microsyringe and 30-gauge needle. Upon assessment, the sciatic nerves into which cancer cells were injected were isolated. When tissue samples were prepared, the nerves were allowed to stand in 4% paraformaldehyde at 4° C. for one whole day and night to fix them. The fixed sciatic nerves were sliced into 3-μm sections, and then immunostained or hematoxylin/eosin-stained to measure the distance of neural invasion. Using an objective micrometer (Sankei Co.), the longitudinal length of the whole tumor was measured in the longitudinally sliced thin sections of the nerves to determine the distance of neural invasion. Tissue mRNA was extracted from tissue samples prepared by crushing with a Multi-Beads Shocker (Yasui Kikai Co.) immediately after harvesting the tissues.

RNA Extraction and Real-Time RT-PCR

Using TRIzol (Life Technologies), total RNA was isolated from cell pellets harvested from dishes, or crushed tissues. cDNA was synthesized from $1 \times 10^3$ ng of total RNA using an ExScript RT reagent Kit (Takara Bio) and Takara PCR Thermal Cycler Dice (Takara Bio) according to the manual recommended by Takara Bio, Inc. Real-time RT-PCR was carried out using Smart Cycler II System (Cepheid) and a SYBR RT-PCR kit (Takara Bio). Primers that can specifically amplify cDNA of the human IL-6a receptor (IL6R), the human IL-6β receptor (gp130), human GAPDH, mouse IL-6, mouse EGF, or mouse GAPDH, were used. The sequences of the primers are shown below:

```
human IL6R:
                                  (SEQ ID NO: 1)
forward, tgagctcagatatcgggctgaac;
and
                                  (SEQ ID NO: 2)
reverse, cgtcgtggatgacacagtgatg;

human gp130:
                                  (SEQ ID NO: 3)
forward, gaagcaagtgggatcacctatgaa;
and
                                  (SEQ ID NO: 4)
reverse, ctgtagccttgagtatgggatgga;

human GAPDH:
                                  (SEQ ID NO: 5)
forward, gcaccgtcaaggctgagaac;
and
                                  (SEQ ID NO: 6)
reverse, atggtggtgaagacgccagt;
```

```
                                          -continued
mouse IL-6:
                                                     (SEQ ID NO: 7)
forward, ccacttcacaagtcggaggctta;
and
                                                     (SEQ ID NO: 8)
reverse, gcaagtgcatcatcgttgttcatac;

mouse EGF:
                                                     (SEQ ID NO: 9)
forward, catcatggtggtggctgtctg;
and
                                                     (SEQ ID NO: 10)
reverse, cacttccgcttggctcatca;

mouse GAPDH:
                                                     (SEQ ID NO: 11)
forward, aaatggtgaaggtcggtgtg;
and
                                                     (SEQ ID NO: 12)
reverse, tgaaggggtcgttgatgg.
```

Quantitation was carried out by the method recommended by Takara Bio.

mRNA Knockdown mRNA expression knockdown was carried out using siRNAs produced by Ambion. The following siRNAs were used: human IL6R siRNA, human gp130 siRNA, and Negative Control #1 siRNA. $2 \times 10^5$ cancer cells were plated in 3.5-cm dishes. After 48 hours of incubation, 20 μM of siRNA and 8 μl of DharmaFECT transfection reagent 4 (Dharmacon) were added to the cells. After 24 hours, the cells were harvested and used for mRNA expression analysis or for preparation of the neural invasion model.

Statistical Analysis

The analysis software used was STATVIEW 5.0. The difference between average values was evaluated by two-sided Student-t test. Error bars in the figures indicate the standard deviation.

Example 1

The mRNA expression of IL-6α receptor (IL6R) and IL-6β receptor (gp130) in cells of the human pancreatic cancer lines was assessed by real-time RT-PCR. It is clearly demonstrated that the human pancreatic cancer lines express IL6R mRNA (FIG. 1A) and gp130 mRNA (FIG. 1B).

Example 2

Figure 2:
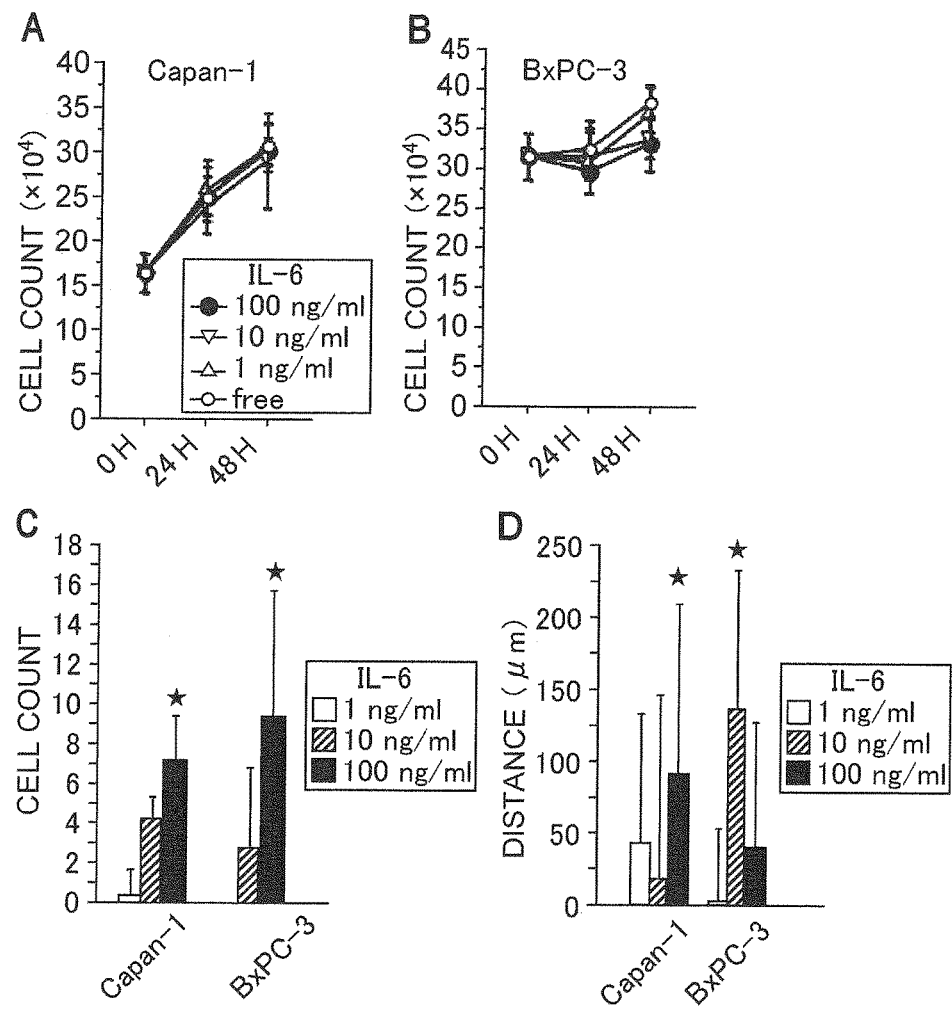
FIG. 2 depicts diagrams showing determination of the effects of IL-6 on growth activity, chemotactic activity, and migratory activity of human pancreatic cancer cell lines using human recombinant IL-6.

Using human recombinant IL-6, the effects of IL-6 on growth activity, chemotactic activity, and migratory activity of the human pancreatic cancer cell lines were assessed by monitoring the cell count over time (FIGS. 2A and 2B), by chemotaxis assay (FIG. 2C), and by wound healing assay (FIG. 2D). It was demonstrated that IL-6 enhances the chemotactic and migratory activities of the pancreatic cancer cell lines, while IL-6 has no effect on the cell growth.

Example 3

Figure 3:
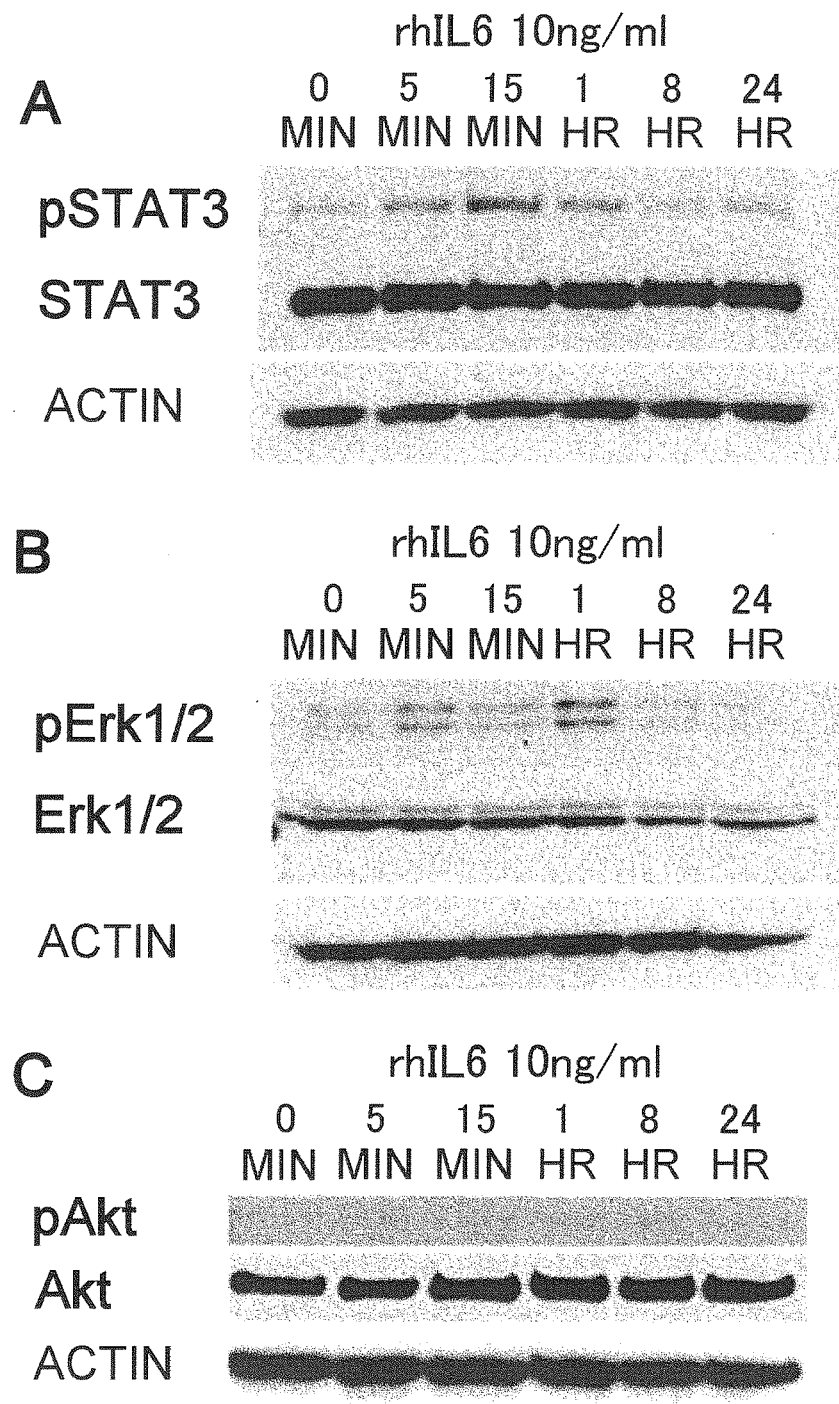
FIG. 3 shows results of assessing the effects of IL-6 on intracellular signaling in the human pancreatic cancer Capan-1 cell line by Western blotting using human recombinant IL-6 (rhIL6).

Using human recombinant IL-6 (rhIL6), the effect of IL-6 on intracellular signaling of the human pancreatic cancer Capan-1 cell line was assessed by Western blotting for phosphorylated STAT3 (pSTAT3) (FIG. 3A), phosphorylated Erk1/2 (pErk1/2) (FIG. 3B), and phosphorylated Akt (pAkt) (FIG. 3C). The intracellular expression levels of phosphorylated STAT3 protein and phosphorylated Erk1/2 proteins were clearly elevated 15 minutes and one hour after addition of rhIL6, respectively. In contrast, IL-6 had no effect on the expression of phosphorylated Akt.

Example 4

Figure 4:
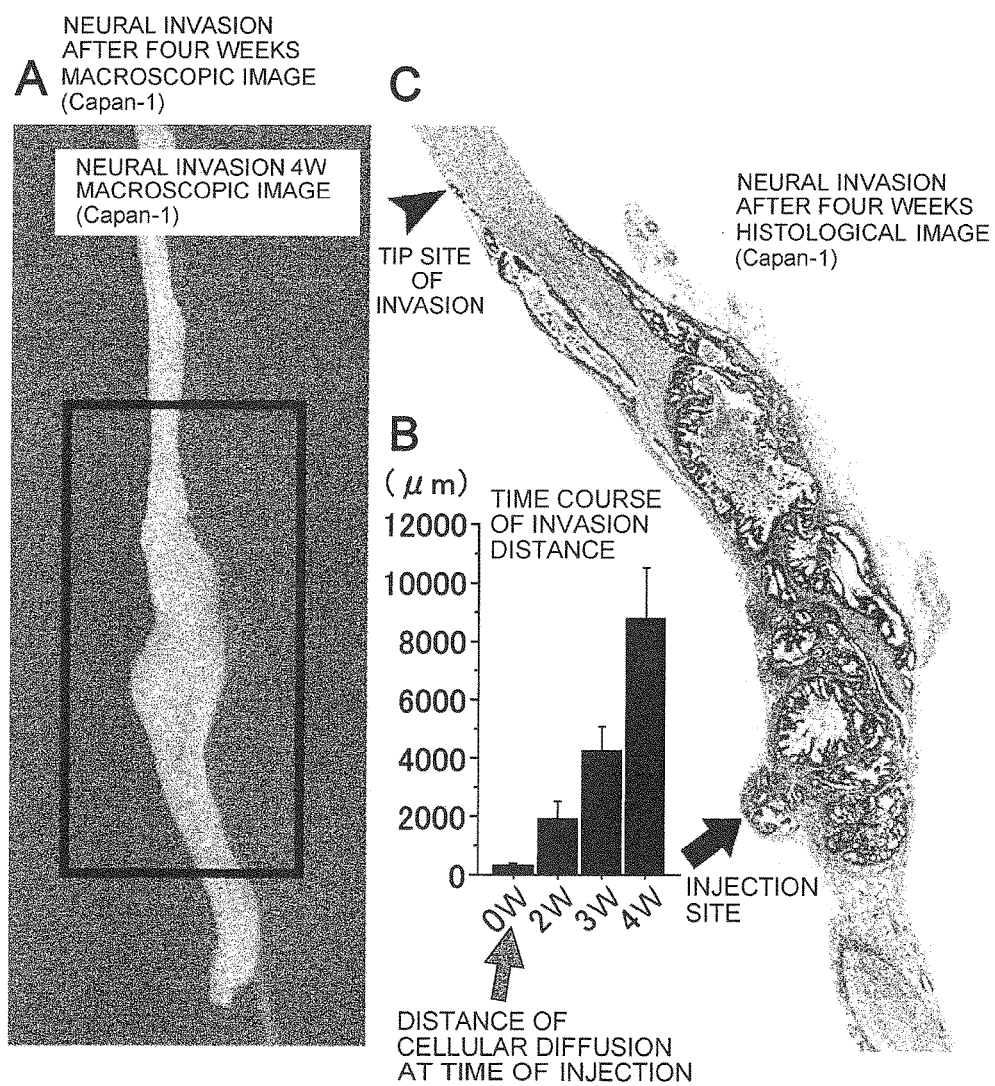
FIG. 4 depicts a graph and photographs showing a mouse model for neural invasion prepared using a human pancreatic cancer cell line.

The distance of neural invasion is an important factor in the mode of invasion of pancreatic cancer. It is essential to create a mouse model for neural invasion that reproduces neural invasion and allows measuring the distance of neural invasion in order to assess therapeutic methods for controlling this vital mode of tumor invasion in pancreatic cancer. A neural invasion model was prepared by directly introducing cells of the human pancreatic cancer Capan-1 cell line into the sciatic nerves of immunodeficient mice. Macroscopically, the nerves had a rough surface at the site of neural invasion, and they were clearly thicker than the normal nerve (FIG. 4A). Histologically, the distance of neural invasion one week after the injection was clearly longer than the distance of intraneural diffusion of injected Capan-1, and the distance was increased over time (FIG. 4B). The neural invasion expanded from the injection site toward the central side (FIG. 4C). These characteristics are similar to those of the neural invasion of human pancreatic cancer.

Example 5

Figure 5:
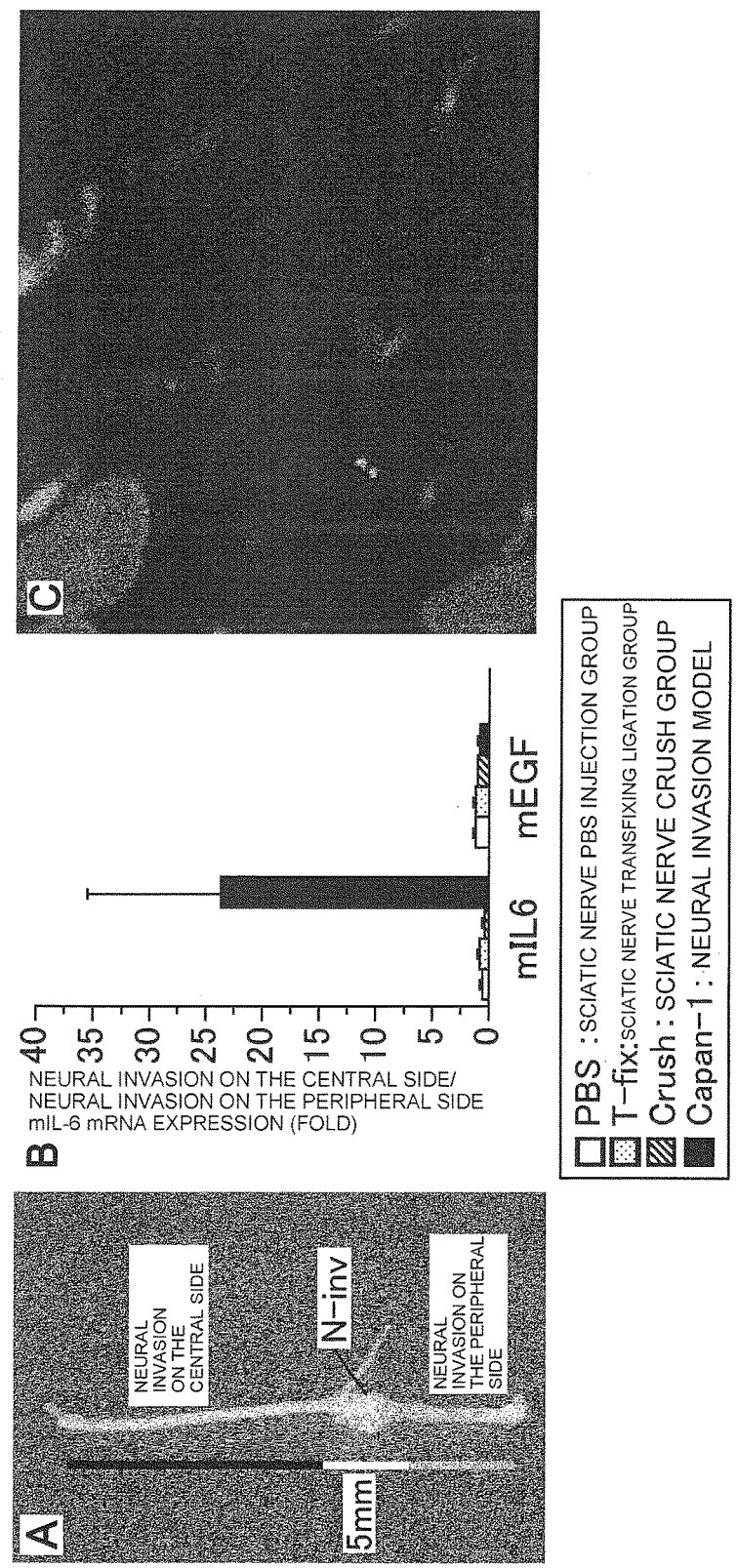
FIG. 5 depicts a graph and photographs showing the distribution of mouse IL-6 expression in the neural invasion model and various models for nerve damage.

The neural invasion of human pancreatic cancer has been reported to damage nerve tissues around the tumor. Such nerve damages are known to enhance IL-6 expression in nerve tissues on the peripheral side of the damage site. To assess the influence of neural invasion on the expression pattern of IL-6 in nerve tissues, mouse IL-6 (mIL6) mRNA expressed in nerve tissues on the central and peripheral sides of the neural invasion site in the neural invasion model was assayed by real-time RT-PCR (FIG. 5B). mIL6 was expressed at a high level in the central side of the neural invasion site. The high expression was not observed in the other nerve damage model animals (FIG. 5B). When the expression of mIL6 protein was assessed by fluorescent immunostaining, IL6-positive granules were found to be present in the same area in which cells are positive for S 100, which is a marker of Schwann cells (FIG. 5C). This shows that, in the neural invasion model, mIL6-secreting cells include Schwann cells. Meanwhile, EGF is known to be expressed at a high level upon nerve damage. However, the expression pattern of mouse EGF (mEGF) mRNA was different from that of mIL6, and the mRNA was not highly expressed on the central side. This finding suggests that IL-6 is closely involved in the tumor/nerve interaction at the site of neural invasion.

Example 6

Figure 6:
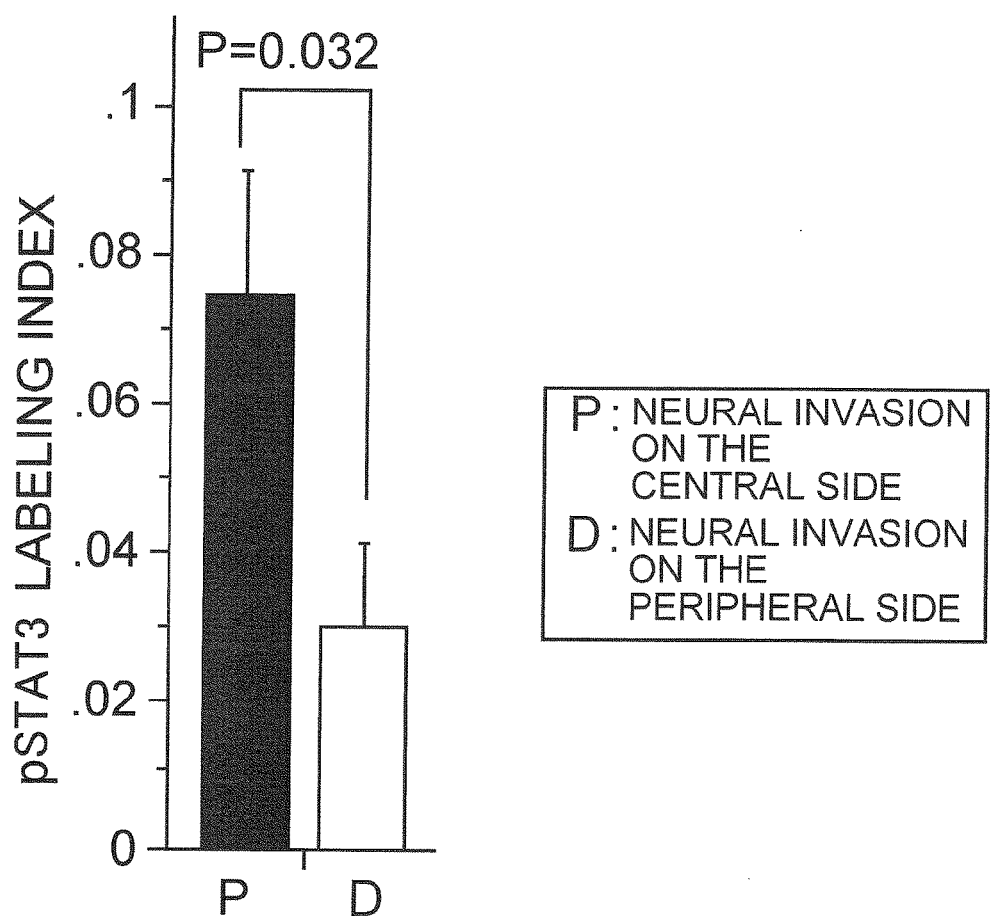
FIG. 6 is a graph showing the expression of phosphorylated STAT3 protein in pancreatic cancer cells at the site of neural invasion.

The expression of phosphorylated STAT3 (pSTAT3) protein, which is important for the intracellular signaling of IL-6, in pancreatic cancer cells was assessed by immunostaining. The expression of phosphorylated STAT3 was found to be enhanced on the central side of the neural invasion site (FIG. 6). This is consistent with the result that the expression of IL-6 is enhanced in nerve tissues on the central side of the neural invasion site.

Example 7

Figure 7:
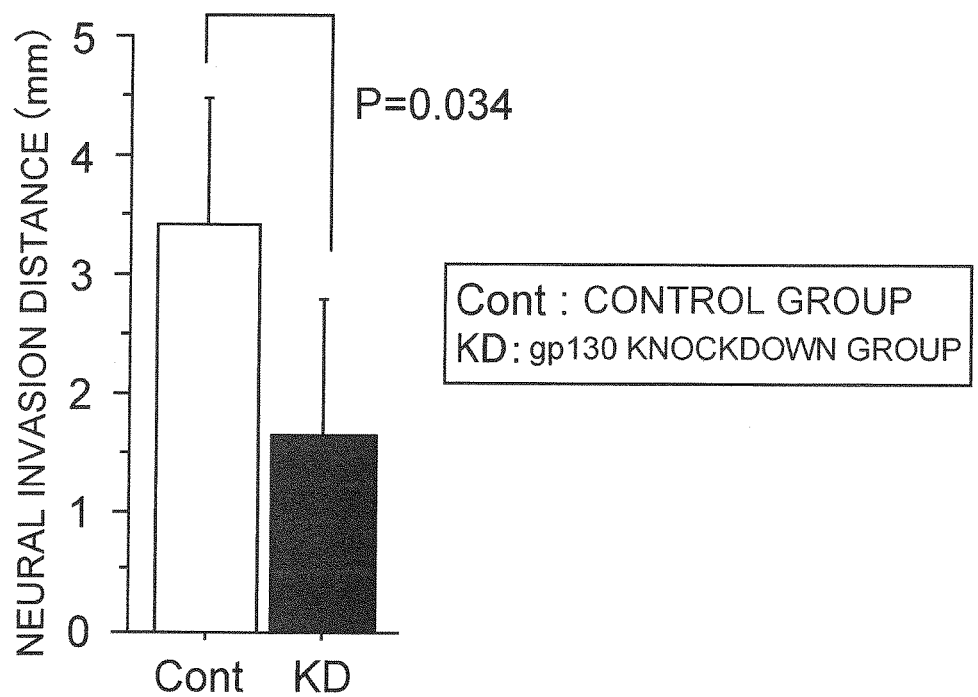
FIG. 7 is a graph showing the effect of 130 knockdown on suppression of the distance of neural invasion.

The action of gp130 is essential for the intracellular signaling of IL-6. Using an siRNA, gp130 mRNA expression was knocked down in a pancreatic cancer cell line. When the neural invasion model was prepared using the knockdown cells, the distance of neural invasion was decreased (FIG. 7). This result shows that signals mediated by gp130 including those derived from IL-6 are essential for neural invasion.

Example 8

Figure 8:
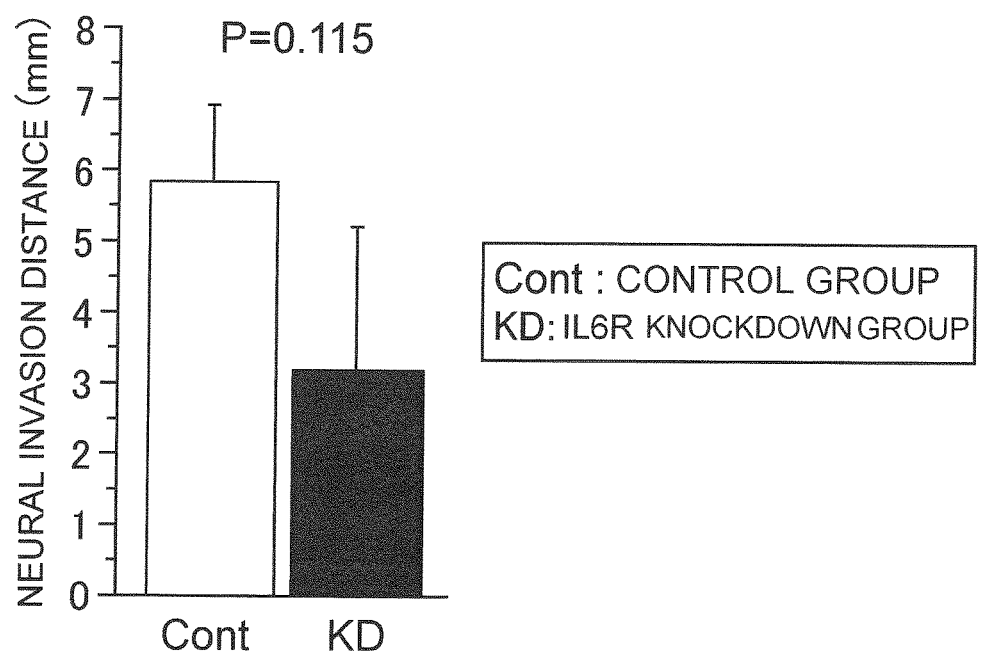
FIG. 8 is a graph showing the effect of IL-6R knockdown on suppression of the distance of neural invasion.

The action of IL-6 receptor (IL6R) is essential for the intracellular signaling of IL-6. Using an siRNA, IL6R mRNA expression was knocked down in a pancreatic cancer cell line. When the neural invasion model was prepared using the knockdown cells, the distance of neural invasion was decreased (FIG. 8). This result shows that signals mediated by IL-6 are essential for neural invasion.

Example 9

Furthermore, a JAK inhibitor or an anti-IL-6 receptor antibody was administered to neural invasion model mice to assess the effect of these inhibitors on neural invasion.

Administration of a JAK Inhibitor to Neural Invasion Model Mice

The JAK inhibitor AG490 (CALBIOCHEM), which inhibits STAT3 phosphorylation, was dissolved in DMSO, and then diluted with physiological saline to prepare an AG490 solution in 1% DMSO. From two days after preparation of the neural invasion model, 0.5 mg of AG490 was administered into the peritoneal cavities of the mice every day. Two weeks after the model preparation, the sciatic nerves into which cancer cells were injected were isolated to determine the distance of neural invasion. For the control group, 1% DMSO was administered in the same manner as described above. The number of mice used was seven in each of the AG490 and DMSO groups.

Administration of an Anti-IL-6 Receptor Antibody to Neural Invasion Model Mice

An anti-IL-6 receptor antibody (tocilizumab; Chugai Pharmaceutical Co.), which inhibits the human IL-6 receptor, was dissolved in physiological saline. One week after preparation of the mouse model for neural invasion, the anti-IL-6 inhibitory antibody was administered to the mice at 5 µg/g twice a week. Three weeks after model preparation, the sciatic nerves into which cancer cells were injected were isolated to determine the distance of neural invasion. For the control group, human IgG (Sigma) dissolved at 5 µg/g in physiological saline was administered in the same manner as described above. The number of mice used was six in the anti-IL-6 receptor antibody group and four in the control group.

Statistical Analysis

The analysis software used was STATVIEW 5.0. The difference between average values was evaluated by two-sided Student-t test. Error bars in the figures indicate the standard deviation.

Figure 9:
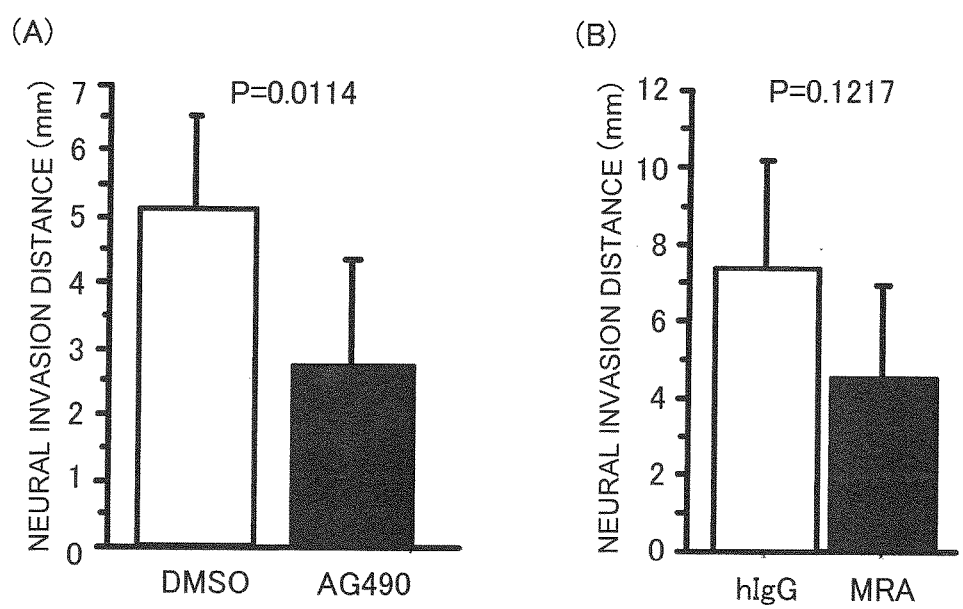
FIG. 9 depicts graphs showing the effects of administration of the JAK inhibitor AG490 or an anti-IL-6 receptor antibody on neural invasion in the mouse model for neural invasion.

From two days after injection of cancer cells, AG490, which inhibits JAK (Janus Kinase) that phosphorylates STAT3 essential for the intracellular signaling of IL-6, was intraperitoneally administered every day for 12 days. This resulted in suppression of neural invasion (FIG. 9A). This finding shows that JAK and STAT which are intracellular signals downstream of IL-6 are essential for neural invasion.

Meanwhile, from one week after injection of cancer cells, an anti-human IL-6 receptor antibody was administered twice a week for two weeks to inhibit the action of human IL-6. This resulted in suppression of neural invasion (FIG. 9B). This finding indicates that neural invasion of human pancreatic cancer was inhibited by the anti-human IL-6 receptor antibody.

INDUSTRIAL APPLICABILITY

The present inventors demonstrated that neural invasion of pancreatic cancer can be suppressed by administering an anti-IL-6 receptor antibody. Furthermore, it was also shown that pancreatic cancer can be treated by administering an anti-IL-6 receptor antibody.

The invention claimed is:

1. A method of reducing the distance of neural invasion of a pancreatic cancer cell in the central direction, which comprises administering a therapeutically effective dose of an anti-IL-6 receptor antibody to a subject in need thereof, wherein the subject has developed neural invasion, wherein the administration results in reduction of the distance of neural invasion in the subject, and wherein the neural invasion is by pancreatic cancer cells.

2. The method of claim 1, wherein the antibody is a chimeric antibody.

3. The method of claim 1, wherein the antibody is a human antibody.

4. The method of claim 1, wherein the antibody is a humanized antibody.

5. The method of claim 4, wherein the antibody is tocilizumab.

6. A method of reducing the distance of neural invasion of a pancreatic cancer cell in the central direction, which comprises administering a therapeutically effective dose of an anti-IL-6 receptor antibody to a subject diagnosed to have neural invasion by the pancreatic cancer cell, and wherein the administration results in reduction of the distance of neural invasion in the subject.

7. The method of claim 6, wherein the antibody is a chimeric antibody.

8. The method of claim 6, wherein the antibody is a human antibody.

9. The method of claim 6, wherein the antibody is a humanized antibody.

10. The method of claim 9, wherein the antibody is tocilizumab.

* * * * *

UNITED STATES PATENT AND TRADEMARK OFFICE
CERTIFICATE OF CORRECTION

PATENT NO. : 10,717,781 B2
APPLICATION NO. : 12/996162
DATED : July 21, 2020
INVENTOR(S) : Mitsunaga et al.

It is certified that error appears in the above-identified patent and that said Letters Patent is hereby corrected as shown below:

On the Title Page

Assignees item (73), please replace "National Cancer Center, Tokyo (JP); Chugai Seiyako Kabushiki Kaisha, Tokyo (JP)" with -- National Cancer Center, Tokyo (JP); Chugai Seiyaku Kabushiki Kaisha, Tokyo (JP) --.

Signed and Sealed this
Fifth Day of January, 2021

Andrei Iancu
*Director of the United States Patent and Trademark Office*